(12) United States Patent
Ito et al.

(10) Patent No.: US 10,266,519 B2
(45) Date of Patent: *Apr. 23, 2019

(54) 1-PYRAZOLYL-3-(4-((2-ANILINOPYRIMIDIN-4-YL) OXY) NAPTHTHALEN-I-YL) UREAS AS P38 MAPKINASE INHIBITORS

(71) Applicant: RESPIVERT LIMITED, Buckinghamshire (GB)

(72) Inventors: Kazuhiro Ito, Wallington (GB); Catherine Elisabeth Charron, London (GB); John King-Underwood, Pendock (GB); Stuart Thomas Onions, Nottingham (GB); Alistair Ian Longshaw, Nottingham (GB); Rudy Broeckx, Beerse (BE); Walter Filliers, Beerse (BE); Alex Copmans, Beerse (BE)

(73) Assignee: RESPIVERT LIMITED, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/812,425

(22) Filed: Nov. 14, 2017

(65) Prior Publication Data
US 2018/0134687 A1 May 17, 2018

Related U.S. Application Data

(63) Continuation of application No. 14/795,957, filed on Jul. 10, 2015, now Pat. No. 9,850,231, which is a continuation of application No. 14/349,345, filed as application No. PCT/GB2012/052445 on Oct. 3, 2012, now Pat. No. 9,108,950.

(30) Foreign Application Priority Data

| Oct. 3, 2011 | (EP) | 11183682 |
| Oct. 3, 2011 | (EP) | 11183688 |
| May 16, 2012 | (EP) | 12168395 |
| May 16, 2012 | (EP) | 12168396 |

(51) Int. Cl.
| C07D 401/14 | (2006.01) |
| C07D 403/12 | (2006.01) |
| A61K 31/4155 | (2006.01) |
| C07D 491/10 | (2006.01) |
| A61K 31/215 | (2006.01) |
| A61K 31/351 | (2006.01) |
| A61K 31/513 | (2006.01) |
| A61K 31/506 | (2006.01) |

(52) U.S. Cl.
CPC .......... *C07D 403/12* (2013.01); *A61K 31/215* (2013.01); *A61K 31/351* (2013.01); *A61K 31/4155* (2013.01); *A61K 31/506* (2013.01); *A61K 31/513* (2013.01); *C07D 491/10* (2013.01); *C07B 2200/13* (2013.01); *Y02A 50/406* (2018.01)

(58) Field of Classification Search
CPC ............... C07D 401/14; C07D 403/12; A61K 31/4155; A61K 31/497
USPC ...................... 544/321, 405; 514/255.05, 274
See application file for complete search history.

(56) References Cited

U.S. PATENT DOCUMENTS

| 6,319,921 | B1 | 11/2001 | Cirillo et al. |
| 6,492,393 | B1 | 12/2002 | Breitfelder et al. |
| 6,492,529 | B1 | 12/2002 | Kapadia et al. |
| 6,525,046 | B1 | 2/2003 | Cirillo et al. |
| 6,583,282 | B1 | 6/2003 | Zhang et al. |
| 6,852,717 | B2 | 2/2005 | Cirillo et al. |
| 6,894,173 | B2 | 5/2005 | Zhang et al. |
| 6,916,814 | B2 | 7/2005 | Moss et al. |
| 7,041,669 | B2 | 5/2006 | Cirillo et al. |
| 7,241,758 | B2 | 7/2007 | Hoa et al. |
| 7,329,670 | B1 | 2/2008 | Dumas et al. |
| 7,384,967 | B2 | 6/2008 | Polisetti et al. |
| 7,511,057 | B2 | 3/2009 | Mathias |
| 7,582,638 | B2 | 9/2009 | De Dios et al. |
| 7,678,811 | B2 | 3/2010 | Dumas et al. |
| 7,700,620 | B2 | 4/2010 | Sutton et al. |
| 7,838,524 | B2 | 11/2010 | Lee et al. |
| 7,838,541 | B2 | 11/2010 | Dumas et al. |
| 7,897,628 | B2 | 3/2011 | Polisetti et al. |
| 8,071,616 | B2 | 12/2011 | Dumas et al. |
| 8,293,748 | B2 | 10/2012 | Ito et al. |
| 8,293,771 | B2 | 10/2012 | Ito et al. |
| 8,299,073 | B2 | 10/2012 | Ito et al. |

(Continued)

FOREIGN PATENT DOCUMENTS

| WO | 1998/057937 A2 | 12/1998 |
| WO | 1999/032110 A1 | 7/1999 |

(Continued)

OTHER PUBLICATIONS

Pimlott, PubMed Abstract (Nucl Med Commun., 26(3):183-8), 2005.*
Hulikal, Deuterium Labeled Compounds in Drug Discovery Process, Abstract, 2010.*
CAS Registry No. 1379397-83-7, 2012 American Chemical Society.
CAS Registry No. 1379547-84-7, 2012 American Chemical Society.
CAS Registry No. 1379462-42-6, 2012 American Chemical Society.

(Continued)

*Primary Examiner* — Deepak R Rao
(74) *Attorney, Agent, or Firm* — McDermott Will & Emery LLP

(57) ABSTRACT

There is provided a compound of formula (I) which is an inhibitor of the family of p38 mitogen-activated protein kinase enzymes, and to its use in therapy, including in pharmaceutical combinations, especially in the treatment of inflammatory diseases, including inflammatory diseases of the lung, such as asthma and COPD.

11 Claims, 7 Drawing Sheets

(56) References Cited

U.S. PATENT DOCUMENTS

| | | | |
|---|---|---|---|
| 8,299,074 B2 | 10/2012 | Ito et al. | |
| 8,541,424 B2 | 9/2013 | DeGoey et al. | |
| 8,546,405 B2 | 10/2013 | DeGoey et al. | |
| 8,618,140 B2 | 12/2013 | Ito et al. | |
| 8,618,289 B2 | 12/2013 | Abraham et al. | |
| 8,642,773 B2 | 4/2014 | Ito et al. | |
| 8,809,343 B2 | 8/2014 | Chen et al. | |
| 8,927,563 B2 | 1/2015 | Fyfe et al. | |
| 8,933,228 B2 | 1/2015 | Murray | |
| 9,108,950 B2 | 8/2015 | Onions et al. | |
| 9,447,076 B2 * | 9/2016 | Longshaw | C07D 401/14 |
| 9,850,231 B2 * | 12/2017 | Ito | C07D 403/12 |
| 9,884,845 B2 * | 2/2018 | Longshaw | C07D 401/14 |
| 2004/0152725 A1 | 8/2004 | Moss et al. | |
| 2006/0035922 A1 | 2/2006 | Mathias et al. | |
| 2007/0078121 A1 | 4/2007 | Flynn et al. | |
| 2008/0300281 A1 | 12/2008 | Dumas et al. | |
| 2009/0131437 A1 | 5/2009 | Furet et al. | |
| 2010/0160355 A1 | 6/2010 | DeGoey et al. | |
| 2010/0168138 A1 | 7/2010 | DeGoey et al. | |
| 2012/0122902 A1 | 5/2012 | Chen et al. | |
| 2012/0244120 A1 | 9/2012 | Charron et al. | |
| 2013/0029990 A1 | 1/2013 | King-Underwood et al. | |
| 2013/0040962 A1 | 2/2013 | King-Underwood et al. | |
| 2013/0040995 A1 | 2/2013 | King-Underwood et al. | |
| 2013/0102607 A1 | 4/2013 | Cass et al. | |
| 2013/0123260 A1 | 5/2013 | Charron et al. | |
| 2014/0057915 A1 | 2/2014 | Cariou et al. | |
| 2014/0114061 A1 | 4/2014 | Kugimoto et al. | |
| 2014/0228410 A1 | 8/2014 | Ito et al. | |
| 2014/0249169 A1 | 9/2014 | Ito et al. | |
| 2014/0296208 A1 | 10/2014 | Baker et al. | |
| 2015/0016648 A1 | 6/2015 | Fyfe et al. | |
| 2015/0203475 A1 | 7/2015 | Duffy et al. | |
| 2015/0210722 A1 | 7/2015 | Fyfe et al. | |
| 2015/0218137 A1 | 8/2015 | Cariou et al. | |
| 2015/0225373 A1 | 8/2015 | Fyfe et al. | |
| 2015/0225427 A1 | 8/2015 | Fyfe et al. | |
| 2015/0232450 A1 | 8/2015 | Longshaw et al. | |
| 2015/0329523 A1 | 11/2015 | Frickel et al. | |
| 2016/0009695 A1 | 1/2016 | Ito et al. | |
| 2016/0016934 A1 | 1/2016 | Fyfe | |
| 2016/0039797 A1 | 2/2016 | Fyfe | |
| 2016/0045482 A1 | 2/2016 | Charron | |
| 2016/0096805 A1 | 4/2016 | Fyfe | |
| 2016/0102059 A1 | 4/2016 | Baker et al. | |
| 2016/0115152 A1 | 4/2016 | King-Underwood et al. | |

FOREIGN PATENT DOCUMENTS

| | | |
|---|---|---|
| WO | 1999/032455 A1 | 7/1999 |
| WO | 2000/043384 A1 | 7/2000 |
| WO | 2001/004115 A2 | 1/2001 |
| WO | 2001/036403 A1 | 5/2001 |
| WO | 2001/064642 A2 | 9/2001 |
| WO | 2002/083628 A1 | 10/2002 |
| WO | 2002/092576 A1 | 11/2002 |
| WO | 2003/005999 A2 | 1/2003 |
| WO | 2003/068228 A1 | 8/2003 |
| WO | 2003/068229 A1 | 8/2003 |
| WO | 2003/072569 A1 | 9/2003 |
| WO | 2004/002481 A1 | 1/2004 |
| WO | 2004/014387 A1 | 2/2004 |
| WO | 2005/110994 A1 | 11/2005 |
| WO | 2005/113556 | 12/2005 |
| WO | 2006/071940 A2 | 7/2006 |
| WO | 2006/072589 A2 | 7/2006 |
| WO | 2007/002635 A2 | 1/2007 |
| WO | 2007/114926 | 10/2007 |
| WO | 2008/067027 A2 | 6/2008 |
| WO | 2010/038085 A2 | 4/2010 |
| WO | 2010/038086 A2 | 4/2010 |
| WO | 2010/067130 A8 | 6/2010 |
| WO | 2010/067131 A1 | 6/2010 |
| WO | 2010/075376 A2 | 7/2010 |
| WO | 2010/075380 A1 | 7/2010 |
| WO | 2010/112936 A1 | 10/2010 |
| WO | 2011/070368 A1 | 6/2011 |
| WO | 2011/070369 A1 | 6/2011 |
| WO | 2011/121366 A1 | 10/2011 |
| WO | 2011/124923 A2 | 10/2011 |
| WO | 2011/124930 A1 | 10/2011 |
| WO | 2011/153553 A2 | 12/2011 |
| WO | 2011/158039 A1 | 12/2011 |
| WO | 2011/158042 A2 | 12/2011 |
| WO | 2011/158044 A2 | 12/2011 |
| WO | 2013/050756 A1 | 4/2013 |
| WO | 2013/050757 A1 | 4/2013 |
| WO | 2014/027209 A1 | 2/2014 |
| WO | 2014/033446 A1 | 3/2014 |
| WO | 2014/033447 A1 | 3/2014 |
| WO | 2014/033448 A1 | 3/2014 |
| WO | 2014/033449 A1 | 3/2014 |
| WO | 2014/076484 | 5/2014 |
| WO | 2014/140582 | 9/2014 |
| WO | 2014/162121 | 10/2014 |
| WO | 2015/121444 | 8/2015 |

OTHER PUBLICATIONS

CAS Registry No. 1379462-36-8, 2012 American Chemical Society.
CAS Registry No. 1379401-24-7, 2012 American Chemical Society.
CAS Registry No. 1384608-34-7, 2012 American Chemical Society.
CAS Registry No. 1384595-05-4, 2012 American Chemical Society.
CAS Registry No. 1384611-77-1, 2012 American Chemical Society.
CAS Registry No. 1384610-90-5, 2012 American Chemical Society.
Onions, et al, 2016, "The discovery of narrow spectrum kinase inhibitors: New therapeutic agents for the treatment of COPD and steroid-resistant asthma," Journal of Medicinal Chemistry; p. 1-70.
To, et al., 2015, "Potent anti-inflammatory effects of the narrow spectrum kinase inhibitor RV1088 on rheumatoid arthritis synovial membrane cells", British Journal of Pharmacology, 172; pp. 3805-3816.
Dumas, et al., 2004, "Recent developments in the discovery of protein kinase inhibitors from the urea class", Current Opinion in Drug Discovery and Develoment 7(5): pp. 600-616.
Exam Report from corresponding Chilean application No. 813-2014 dated Jul. 22, 2016.
O'Keefe, S.J. et al., "Chemical Genetics Define the Roles of p38alpha and p38beta in Acute and Chronic Inflammation" J. Biol. Chem., 2007, 282(48):34663-71.
Fitzsimmons, B.L. et al., "Role of spinal p38alpha and MAPK in inflammatory hyperalgesia and spinal COX-2 expression", Neuroreport, 2010, 21(4):313-7.
Pettus et al., Small Molecule p38 MAP Kinase Inhibitors for the Treatment of Inflammatory Diseases: Novel Structures and Developments During 2006-2008 Curr. Top. Med. Chem., 2008, 8(16):1452-67.
Shmueli, O. et al., "GeneNote: whole genome expression profiles in normal human tissues", Comptes Rend.us Biologies, 2003, 326(10-11):1067-1072/Genecard.
Smith, S. et al., "Inhibitory effect of p38 mitogen-activated protein kinase inhibitors on cytokine release from human macrophages", J. Br. J. Pharmacol., 2006, 149:393-404.
Hale, K. K. et al., "Differential Expression and Activation of p38 Mitogen-Activated Protein Kinase alpha, beta, gamma and delta in Inflammatory Cell Lineages", J. Immunol., 1999, 162(7):4246-52.
Wang, X. S. et al., "Molecular Cloning and Characterization of a Novel p38 Mitogen-activated Protein Kinase", J. Biol. Chem., 1997, 272(38):23668-23674.
Court, N. W. et al., "Cardiac Expression and Subcellular Localization of the p38 Mitogen-activated Protein Kinase Member, Stress-activated Protein Kinase-3 (SAPK3)", J. Mal. Cell. Cardiol., 2002, 34(4):413-26.

(56) References Cited

OTHER PUBLICATIONS

Mertens, S. et al., "SAP kinase-3, a new member of the family of mammalian stress-activated protein kinases", FEES Lett., 1996, 383(3):273-6.
Chung, F., "p38 Mitogen-Activated Protein Kinase Pathways in Asthma ad COPD", Chest, 2011, 139 (6):1470-1479.
Kuma, Y. "BIRB796 inhibits all p38 MAPK isoforms in vitro and in vivo", J. Biol. Chem., 2005, 280:19472-19479.
Underwood D.C. et al., "SB239063, a p38 MAPK inhibitor, reduces neutrophilia, inflammatory cytokines, MMP-9, and fibrosis in lung", Am. J. Physiol. Lung Cell. Mal. Physiol., 2000, 279:895-902.
Nath, P. et al., "Importance of p38 mitogen-activated protein kinase pathway in allergic airway remodeling and bronchial hyperresponsiveness", Eur. J. Pharmacol., 2006, 544:160-167.
Irusen, E. et al., "p38 Mitogen-activated protein kinase-induced glucocorticoid receptor phosphorylation reduces its activity: Role in steroid-insensitive asthma", J. Allergy Clin. Immunol., 2002, 109:649-657.
Lee et al., "MAP Kinase p38 Inhibitors: Clinical Results and an Intimate Look at Their Interactions with p38a Protein", Current Med. Chem., 2005, 12:2979-2994.
Mercado, N., et al., "p38 Mitogen-Activated Protein Kinase-y Inhibition by Long-Acting Adrenergic Agonists Reversed Steroid Insensitivity in Severe Asthma", Mal. Pharmacol., 2011, 80(6):1128-1135.
Medicherla S. et al., "p38a-Selective Mitogen-Activated Protein Kinase Inhibitor SD-282 Reduces Inflammation in a Subchronic Model of Tobacco Smoke-Induced Airway Inflammation", J. Pharm. Exp. Ther., 2008, 324:921-929.
Papadopoulos, N.G., et al., "Mechanisms of rhinovirus-induced asthma", Paediatr. Respir. Rev,. 2004, 5 (3):255-260.
Grunbgerg, K., et al., :Rhinovirus-induced Airway Inflammation in Asthma, Am. J. Respir. Crit. Care Med., 2001, 164(10):1816-1822.
Wat, D., et al., "The role of respiratory viruses in cystic fibrosis", J. Cyst. Fibros,. 2008, 7:320-328.
Liu, M., et al., "Respiratory viral infections within one year after pediatric lung transplant", Transpl. Infect. Dis,. 2009, 11(4):304-312.
Laza-Stanca, V., et al., "Rhinovirus-induced lower respiratory illness is increased in asthma and related to virus load and Th 1h cytokine and IL-10 production", PNAS, 2008; 105(36): 13562-13567.
Gerna, G., Piralla, A., et al., "Correlation of Phinovirus Load in the Respiratory Tract and Clinical Symptoms in Hospitalized Immunocopetent and Immunocomprised Patients", J. Med. Viral,. 2009, 81(8):1498-1507.
Oliver, B.G., et al., "Rhinovirus exposure impairs immune responses to bacterial products in human alveolar macrophages", Thorax, 2008, 63 :519-525.
Wang, J.H., "Rhinovirus Enhances Various Bacterial Adhesions to Nasal Epithelial Cells Simultaneously", The Larynoscope, 2009, 119(7):1406-1411.
Peleg, A.Y., et al., "Common infections in diabetes:pathogenesis, management and relationship to glycaemic control" Diabetes Metab. Res. Rev., 2007, 23(1):3-13.
Kornum et al., "Diabetes, Glycemic Control, and Risk of Hospitalization with Pneumonia", Diabetes Care, 2008, 31(8):1541-1545.
Rollinger, J.M. et al., "The Human Rhinovirus: Human-Pathological Impact, Mechanisms of Antirhinoviral Agents, and Strategies for Their Discovery", Med. Res. Rev., 2010, Doi 10.1002/med.20176.
Ludwig, S, "Influenza viruses and MAP kinase cascades—Novel targets for an antiviral intervention", 2007; Si>Znal Transduction, 7:81-88.
Shin, Y.K., Liu, Q. et al., "Influenza A virus NSI protein activates the phosphatidylinositol 3-kinase (PI3K)/Akt pathway by direction interaction with the p85 subunit of PI3K", J. Gen. Viral., 2007, 88:13-18.
Ehrhardt, C., Marjuki, H. et al., "Bivalent role of th ephosphatidylinostiol-3-kinase (PI3K) during influrnza virus infection and host cell defence", Cell Microbial., 2006, 8:1336-1348.
Ludwig, S., et al., "MEK inhibition impairs influenza B virus propagation without emergence of resistant variants", FEES Lett., 2004, 561(1-3):37-43.
Sanderson, M.P., et al., "Syk: A Novel Target for Treatment of Inflammation in Lung Disease", Injlamm. Allergy Drug Targets, 2009, 8:87-95.
Lau, C. et al., "Syk Associates with Clathrin and Mediates Phosphatidylinositol 3-Kinase Activation during Human Rhinovirus Intemationlaztion", J. Immunology, 2008, 180(2):870-880.
Bentley, J.K., et al., "Rhinovirus Activates Interleukin-8 Expression via a Src/pl 10 Phosphatidylinositol 3-Kinase/Akt Pthway in Human airway Epithelial Cells", J. Viral., 2007, 81:1186-1194.
Inoue, D. et al, "Mechanisms of mucin production by rhinovirus infection in cultured human airway epithelial cells", Respir. Physiol. Neurobiol., 2006, 154(3):484-499.
Schreiber, S. et al., "Oral p38 Mitogen-Activated Protein Kinase Inhibition with BIRB 796 for Active Crohn's Disease: A Randomized, Double Blind, Placdbo-Controlled Trial", Clin. Gastro. Hepatology, 2006, 4:325-334.
Shilo, Y., "ATM and Related Protein Kinases: Safeguarding Genome Integrity" Nature Reviews Cancer, 2003, 3:155-168.
Olaharsky, A.J. et al., "Identification of a Kinase Profile that Predicts Chromosome Damage Induced by Small Molecule Kinase Inhibitors", PLoS Comput. Biol., 2009, 5(7):e1000446.
Tighe, A. et al., "GSK-3 inhibitors induce chromosome instability", BMC Cell Biology, 2007, 8:34.
Pargellis, C. et al., "Inhibition of p38 MAP kinase by utilizing a novel allosteric binding site", Nature Struct. Biol., 2002, 9(4):268-272.
Fabian, M.A. et al., "A small molecule-kinase interaction map for clinical kinase inhibitors", Nature Biotechnology, 2005, 23 :329-336.
Muehlbauer P.A. et al., "Measuring the mitotic index in chemically-treated human lymphocyte cultures by flow cytomertry", Mutation Research, 2003, 537: 117-130.
Regan, et al., "Pyrazole Urea-Based Inhibitors of p38 MAP Kinase: From Lead Companies to Clinical Candidate", J. Med. Chem. 2002, 45, 2994-3008.
Moss et al., "New modifications to the area of pyrazole-naphthyl urea based 38 MAP kinase inhibitors that bind to the adenine/ATP site", Biooganic & Medicinal Chemistry Letters 2007, 17, 4242-4247.
Cirillo et al., "Discovery and characterization of the N-phenyl-N'-naphthylurea class of p38 kinase inhibitors" Bioorganic & Medicinal Chemistry Letters 2009, 19, 2386-2391.
Boehm et al., "New Inhibitors of p38 Kinase", Expert Opinion in Therapeutic Patents 10(1); pp. 25-37, 2000.
Dodeller et al., "The p38 mitogen-activated protein kinase signaling cascade in CD4 T Cells", Arthritis Research & Therapy, vol. 8, No. 2 (2006). Online at http://arthritis-research.com/content/8/2/205.
Douglas, Jr. "Introduction to Viral Diseases", Cecil Textbook of Medicine, 20th Edition, vol. 2, pp. 1739-1747, 1996.
Gura et al., "Systems for Identifying New Drugs Are Often Faulty", Science, 278: pp. 1041-1042, 1997.
Johnson et al., "Relationships Between Drug Activity in NCI Preclinical In Vitro and In Vivo Models and Early Clinical Trials", British Journal of Cancer, 84(10):pp. 1424-1432, 2008.
Pearce et al., "Failure Mode in Anticancer Drug Discovery and Development", Cancer Drug Design and Discovery Edited by Stephen Deidle, Chapter 18, pp. 424-435, 2008.
Simone, Oncology: Introduction, 20th Edition, vol. 1 DD. 1004-1010, 1996.
U.S. Appl. No. 14/422,158, US 20150218137 A1; Aug. 6, 2015.
U.S. Appl. No. 14/424,240, US 20150225427 A1; Aug. 13, 2015.
U.S. Appl. No. 14/424,627, US 20150225373 A1; Aug. 13, 2015.
U.S. Appl. No. 14/424,361, US 20150203475 A1; Jul. 23, 2015.
U.S. Appl. No. 14/424,967, US 20150210722 A1; Jul. 30, 2015.
U.S. Appl. No. 14/626,548, US 20150016648 A1; Jun. 18, 2015.

* cited by examiner

1-PYRAZOLYL-3-(4-((2-ANILINOPYRIMIDIN-4-YL)OXY) NAPTHTHALEN-I-YL) UREAS AS P38 MAPKINASE INHIBITORS

RELATED APPLICATIONS

The present application is a continuation of U.S. patent application Ser. No. 14/795,957, filed on Jul. 10, 2015, which is a continuation of U.S. patent application Ser. No. 14/349,345, filed on Apr. 3, 2014, which is the U.S. National Stage of International Application No. PCT/GB2012/052445, filed on Oct. 3, 2012, which claims the benefit of European Patent Application No. 11183682.1, filed on Oct. 3, 2011, European Patent Application No. 11183688.8, filed on Oct. 3, 2011, European Patent Application No. 12168396.5, filed on May 16, 2012 and European Patent Application No. 12168395.7, filed on May 16, 2012, the entirety of each of which is incorporated herein by reference.

FIELD OF THE INVENTION

The invention relates to compounds which are inhibitors of the family of p38 mitogen-activated protein kinase enzymes (referred to herein as p38 MAP kinase inhibitors), for example the alpha and gamma kinase sub-types thereof, and of Syk kinase and the Src family of tyrosine kinases, and to their use in therapy, including in pharmaceutical combinations, especially in the treatment of inflammatory diseases, in particular inflammatory diseases of the lung, such as asthma and COPD, as well as those of the gastrointestinal tract, such as ulcerative colitis and Crohn's disease and of the eye, such as uveitis.

BACKGROUND OF THE INVENTION

Four p38 MAPK isoforms (alpha, beta, gamma and delta respectively), have been identified each displaying different patterns of tissue expression in man. The p38 MAPK alpha and beta isoforms are found ubiquitously in the body, being present in many different cell types. The alpha isoform is well characterized in terms of its role in inflammation. Although studies using a chemical genetic approach in mice indicate that the p38 MAPK beta isoform does not play a role in inflammation (O'Keefe, S. J. et al., *J. Biol. Chem.*, 2007, 282(48):34663-71.), it may be involved in pain mechanisms through the regulation of COX2 expression (Fitzsimmons, B. L. et al., *Neuroreport*, 2010, 21(4):313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16):1452-67.). As these adverse effects vary with chemotype, and the compounds have distinct kinase selectivity patterns, the observed toxicities may be structure-related rather than p38 mechanism-based.

Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+ T cells and in endothelial cells (Shmueli, O. et al., *Comptes Rendus Biologies*, 2003, 326(10-11):1067-1072; Smith, S. J. Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the distribution of p38 MAPK gamma although it is expressed more highly in brain, skeletal muscle and heart, as well as in lymphocytes and macrophages (Shmueli, O. et al., *Comptes Rendus Biologies*, 2003, 326(10-11):1067-1072; Hale, K. K., *J. Immunol.*, 1999, 162(7):4246-52; Court, N. W. et al., *J. Mol. Cell. Cardiol.*, 2002, 34(4):413-26; Mertens, S. et al., *FEBS Lett.*, 1996, 383(3):273-6.).

Selective small molecule inhibitors of p38 MAPK gamma and p38 MAPK delta are not currently available, although one previously disclosed compound, BIRB 796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y., *J. Biol. Chem.*, 2005, 280:19472-19479.). In addition BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and in COPD (Chung, F., Chest, 2011, 139(6):1470-1479.). There is now an abundant literature which demonstrates that p38 MAP kinase is activated by a range of pro-inflammatory cytokines and that its activation results in the recruitment and release of additional pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs.

The use of inhibitors of p38 MAP kinase in the treatment of chronic obstructive pulmonary disease (COPD) has also been proposed. Small molecule inhibitors targeted to p38 MAPK α/β have proved to be effective in reducing various parameters of inflammation in cells and in tissues obtained from patients with COPD, who are generally corticosteroid insensitive, (Smith, S. J., Br. J. Pharmacol., 2006, 149:393-404.) as well as in various in vivo animal models (Underwood, D. C. et al., *Am. J. Physiol.*, 2000, 279:L895-902; Nath, P. et al., *Eur. J. Pharmacol.*, 2006, 544:160-167.). Irusen and colleagues have also suggested the possible involvement of p38 MAPK α/β with corticosteroid insensitivity via the reduction of binding affinity of the glucocorticoid receptor (GR) in nuclei (Irusen, E. et al., *J. Allergy Clin. Immunol.*, 2002, 109:649-657.). Clinical experience with a range of p38 MAP kinase inhibitors, including AMG548, BIRB 796, VX702, SCI0469 and SCI0323 has been described (Lee, M. R. and Dominguez, C., *Current Med. Chem.*, 2005, 12:2979-2994.).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., *Mol. Pharmacol.*, 2011, 80(6):1128-1135.) demonstrates that silencing p38 MAPK γ has the potential to restore sensitivity to corticosteroids. Consequently there may be a dual benefit for patients in the use of a p38 MAP kinase inhibitor for the treatment of COPD and severe asthma. However, the major obstacle hindering the utility of p38 MAP kinase inhibitors in the treatment of human chronic inflammatory diseases has been the severe toxicity observed in patients resulting in the withdrawal from clinical development of many compounds including all those specifically mentioned above.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiological investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G., Papi, A., Psarras, S. and Johnston, S. L., *Paediatr. Respir. Rev.*, 2004, 5(3):255-260.). A variety of additional studies support the conclusion that a viral infection can precipitate exacerbations and increase disease severity. For example, experimental clinical infections with rhinovirus have been reported to cause bronchial hyper-responsiveness to histamine in asthmatics that is unresponsive to treatment with corticosteroids (Grunberg, K., Sharon, R. F., et al., *Am. J. Respir. Crit. Care Med.*, 2001, 164(10):1816-1822.). Further evidence derives from the association observed between disease exacerbations in patients with cystic fibrosis and HRV infections (Wat, D., Gelder, C., et al., *J. Cyst. Fibros.*, 2008, 7:320-328.). Also consistent with this body of data is the finding that respiratory viral infections, including rhinovirus, represent an independent risk factor that correlates negatively with the 12 month survival rate in paediatric, lung transplant recipients (Liu, M., Worley, S., et al., *Transpl. Infect. Dis.*, 2009, 11(4):304-312.).

Clinical research indicates that the viral load is proportionate to the observed symptoms and complications and, by implication, to the severity of inflammation. For example, following experimental rhinovirus infection, lower respiratory tract symptoms and bronchial hyper-responsiveness correlated significantly with virus load (Message, S. D., Laza-Stanca, V., et al., *PNAS*, 2008; 105(36):13562-13567.). Similarly, in the absence of other viral agents, rhinovirus infections were commonly associated with lower respiratory tract infections and wheezing, when the viral load was high in immunocompetent paediatric patients (Gerna, G., Piralla, A., et al., *J. Med. Virol.*, 2009, 81(8):1498-1507.).

Interestingly, it has been reported recently that prior exposure to rhinovirus reduced the cytokine responses evoked by bacterial products in human alveolar macrophages (Oliver, B. G., Lim, S., et al., *Thorax*, 2008, 63:519-525.). Additionally, infection of nasal epithelial cells with rhinovirus has been documented to promote the adhesion of bacteria, including *S. aureus* and *H. influenzae* (Wang, J. H., Kwon, H. J. and Yong, J. J., *The Laryngoscope*, 2009, 119(7):1406-1411.). Such cellular effects may contribute to the increased probability of patients suffering a lower respiratory tract infection following an infection in the upper respiratory tract. Accordingly, it is therapeutically relevant to focus on the ability of novel interventions to decrease viral load in a variety of in vitro systems, as a surrogate predictor of their benefit in a clinical setting.

High risk groups, for whom a rhinovirus infection in the upper respiratory tract can lead to severe secondary complications, are not limited to patients with chronic respiratory disease. They include, for example, the immune compromised who are prone to lower respiratory tract infection, as well as patients undergoing chemotherapy, who face acute, life-threatening fever. It has also been suggested that other chronic diseases, such as diabetes, are associated with a compromised immuno-defence response. This increases both the likelihood of acquiring a respiratory tract infection and of being hospitalised as a result (Peleg, A. Y., Weerarathna, T., et al., *Diabetes Metab. Res. Rev.*, 2007, 23(1): 3-13; Kornum, J. B., Reimar, W., et al., *Diabetes Care*, 2008, 31(8):1541-1545.).

Whilst upper respiratory tract viral infections are a cause of considerable morbidity and mortality in those patients with underlying disease or other risk factors; they also represent a significant healthcare burden in the general population and are a major cause of missed days at school and lost time in the workplace (Rollinger, J. M. and Schmidtke, M., *Med. Res. Rev.*, 2010, Doi 10.1002/med.20176.). These considerations make it clear that novel medicines, that possess improved efficacy over current therapies, are urgently required to prevent and treat rhinovirus-mediated upper respiratory tract infections. In general the strategies adopted for the discovery of improved antiviral agents have targeted various proteins produced by the virus, as the point of therapeutic intervention. However, the wide range of rhinovirus serotypes makes this a particularly challenging approach to pursue and may explain why, at the present time, a medicine for the prophylaxis and treatment of rhinovirus infections has yet to be approved by any regulatory agency.

Viral entry into the host cell is associated with the activation of a number of intracellular signalling pathways which are believed to play a prominent role in the initiation of inflammatory processes (reviewed by Ludwig, S, 2007; *Signal Transduction*, 7:81-88.) and of viral propagation and subsequent release. One such mechanism, which has been determined to play a role in influenza virus propagation in vitro, is activation of the phosphoinositide 3-kinase/Akt pathway. It has been reported that this signalling pathway is activated by the NS1 protein of the virus (Shin, Y. K., Liu, Q. et al., *J. Gen. Virol.*, 2007, 88:13-18.) and that its inhibition reduces the titres of progeny virus (Ehrhardt, C., Marjuki, H. et al., *Cell Microbiol.*, 2006, 8:1336-1348.).

Furthermore, the MEK inhibitor U0126 has been documented to inhibit viral propagation without eliciting the emergence of resistant variants of the virus (Ludwig, S., Wolff, T. et al., *FEBS Lett.*, 2004, 561(1-3):37-43.). More recently, studies targeting inhibition of Syk kinase have demonstrated that the enzyme plays an important role in mediating rhinovirus entry into cells and also virus-induced inflammatory responses, including ICAM-1 up-regulation (Sanderson, M. P., Lau, C. W. et al., *Inflamm. Allergy Drug Targets*, 2009, 8:87-95.). Syk activity is reported to be controlled by c-Src as an upstream kinase in HRV infection (Lau, C. et al., *J. Immunol.*, 2008, 180(2):870-880.). A small number of studies have appeared that link the activation of cellular Src (Src1 or p60-Src) or Src family kinases to infection with viruses. These include a report that adenovirus elicits a PI3 kinase mediated activation of Akt through a c-Src dependent mechanism. It has also been suggested that Rhinovirus-39 induced IL-8 production in epithelial cells depends upon Src kinase activation (Bentley, J. K., Newcomb, D. C., *J. Virol.*, 2007, 81:1186-1194.). Finally, it has been proposed that activation of Src kinase is involved in the induction of mucin production by rhinovirus-14 in epithelial cells and sub-mucosal glands (Inoue, D. and Yamaya, M., *Respir. Physiol. Neurobiol.*, 2006, 154(3):484-499.).

It has been disclosed previously that compounds that inhibit the activity of both c-Src and Syk kinases are effective agents against rhinovirus replication (Charron, C. E. et al., WO 2011/158042.) and that compounds that inhibit p59-HCK are effective against influenza virus replication (Charron, C. E. et al., WO 2011/070369.). For the reasons summarised above, compounds designed to treat chronic respiratory diseases that combine these inherent properties with the inhibition of p38 MAPKs, are expected to be particularly efficacious.

Certain p38 MAPK inhibitors have also been described as inhibitors of the replication of respiratory syncitial virus (Cass, L. et al., WO 2011/158039.).

Furthermore, it is noteworthy that a p38 MAPK inhibitor was found to deliver benefit for patients with IBD after one week's treatment which was not sustained over a four week course of treatment (Schreiber, S. et al., *Clin. Gastro. Hepatology*, 2006, 4:325-334.).

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y. *Nature Reviews Cancer*, 2003, 3:155-168.) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.*, 2009, 5(7):e1000446.). Micronucleus formation is implicated in, or associated with, disruption of mitotic processes and is therefore an undesirable manifestation of potential toxicity. Inhibition of glycogen synthase kinase 3α (GSK3α) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology*, 2007, 8:34.).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetectable activity against these off-target enzymes and consequently elicit little or no disruption of mitotic processes, as measured from mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. An objective of the present invention therefore, is to provide such novel compounds that inhibit the enzyme activity of p38 MAP kinase, for example with certain sub-type specificities, together with Syk kinase and tyrosine kinases within the Src family (particularly c-Src) thereby possessing good anti-inflammatory properties, and suitable for use in therapy.

The Compound (I) exhibits a longer duration of action and/or persistence of action in comparison to the previously disclosed allosteric p38 MAP kinase inhibitor BIRB 796 (Pargellis, C. et al., *Nature Struct. Biol.*, 2002, 9(4):268-272.). An additional embodiment provides such novel compound in one or more solid, crystalline forms that possess high chemical and physical stability suitable for formulation as inhaled medicaments.

SUMMARY OF THE INVENTION

Thus in one aspect of the invention there is provided a compound of formula (I):

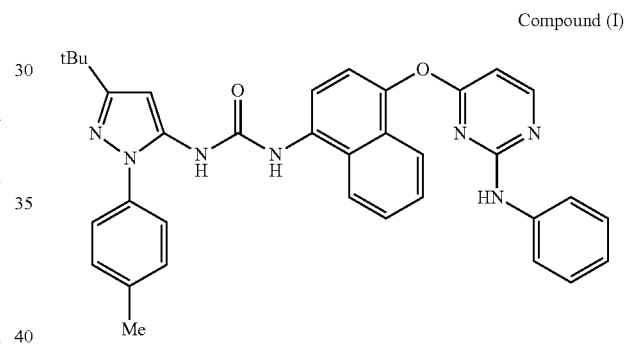

Compound (I)

or a pharmaceutically acceptable salt or solvate thereof, including all stereoisomers and tautomers thereof.

"Compound of formula (I)" may also be referred to herein as "Compound (I)".

In another aspect of the invention there is provided Compound (I) as defined above as the free base.

In another aspect of the invention there is provided Compound (I) as defined above as the anhydrous free base.

In another aspect of the invention there is provided Compound (I) as defined above as the anhydrous free base in solid crystalline form.

In a further aspect of the invention there is provided Compound (I) as defined above as the anhydrous free base in solid crystalline polymorphic form A.

In a further aspect of the invention there is provided Compound (I) as defined above as the anhydrous free base in solid crystalline polymorphic form B.

DETAILED DESCRIPTION OF THE INVENTION

Figure 1:
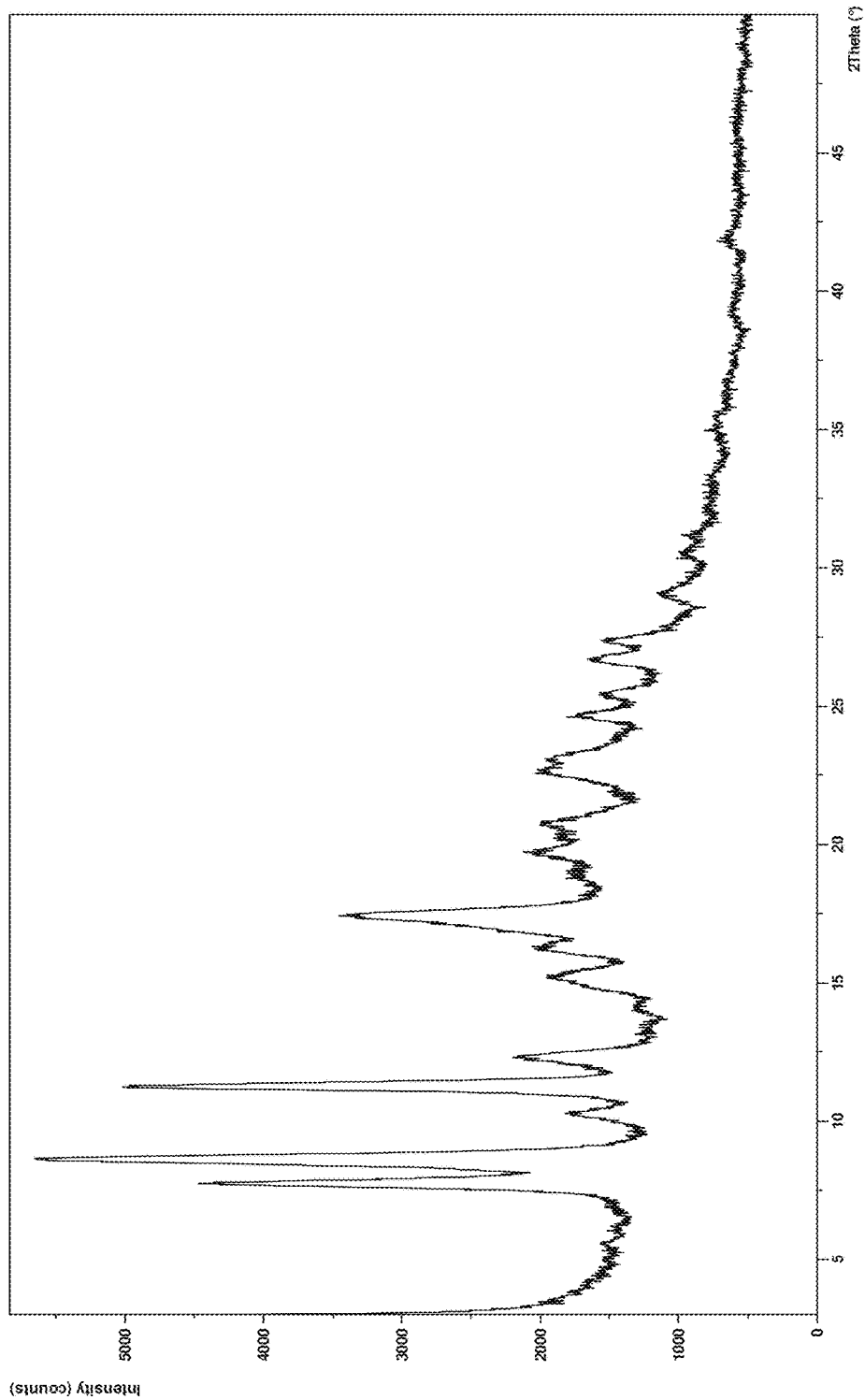
FIG. 1 shows an X-ray powder diffraction (XRPD) pattern obtained from a sample of Compound (I) as the anhydrous free base in solid crystalline polymorphic form A.

The compound of formula (I) disclosed herein is: 1-(3-tert-butyl-1-p-tolyl-1H-pyrazol-5-yl)-3-(4-(2-(phenylamino)pyrimidin-4-yloxy)naphthalen-1-yl)urea.
Examples of salts of Compound (I) include all pharmaceutically acceptable salts, such as, without limitation, acid addition salts of strong mineral acids such as HCl and HBr salts and addition salts of strong organic acids such as methanesulfonic acid.

As employed herein below the definition of a compound of formula (I) is intended to include salts, solvates, and all tautomers of said compound, unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

The invention embraces all isotopic derivatives of Compound (I). Thus the invention embraces compounds which are compounds of Compound (I) having one or more atoms that have been replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Thus the compounds of the disclosure include those where the atom specified is a naturally occurring or non-naturally occurring isotope. In one embodiment the isotope is a stable isotope. Thus the compounds of the disclosure include, for example deuterium containing compounds and the like. Thus, in one embodiment of the invention Compound (I) contains an enriched level of deuterium in one or more hydrogen atoms (e.g. for a given hydrogen atom the level of the deuterium isotope exceeds 20%, 50%, 75%, 90%, 95% or 99% by number). Examples of other isotopes that can be incorporated into Compound (I) or enriched in Compound (I) include isotopes of hydrogen, carbon, nitrogen, oxygen, fluorine, iodine and chlorine such as $^3H$, $^{11}C$, $^{13}C$, $^{14}C$, $^{15}N$, $^{18}F$, $^{123}I$ or $^{125}I$, which may be naturally occurring or non-naturally occurring isotopes.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from 0-dealkylation.

The disclosure also extends to all polymorphic forms of the compounds herein defined.

A route suitable for the preparation of the compound of formula (I) is shown below (Scheme 1).

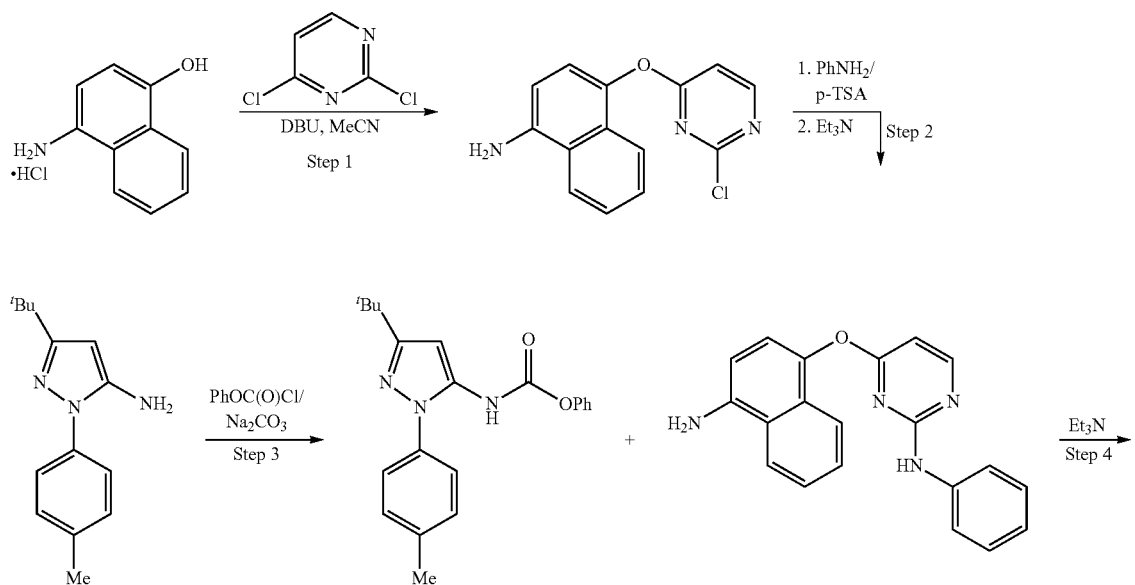

-continued

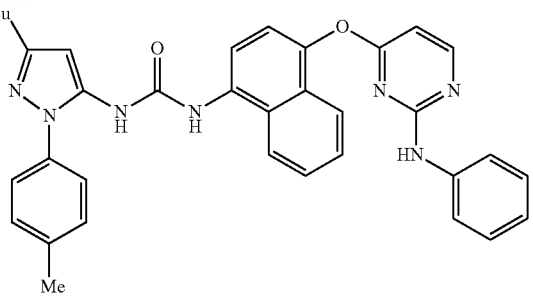

Compound (I)

Protective groups may be required to protect chemically sensitive groups during one or more of the reactions described above, to ensure that the process can be carried out and/or is efficient. Thus if desired or necessary, intermediate compounds may be protected by the use of conventional protective groups. Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

A detailed preparation of Compound (I) is provided in Example 1.

Novel intermediates as described herein form an aspect of the invention.

In another aspect of the invention, there is provided Compound (I) as the anhydrous free base in solid, crystalline form. In a further aspect of the invention, there is provided Compound (I) as the anhydrous free base in solid, crystalline, polymorphic form A which may be obtained, for example, by crystallising Compound (I) from isopropyl acetate. In a particular aspect of the invention, there is provided Compound (I) as the anhydrous free base in solid, crystalline, polymorphic form B, which may be obtained, for example, by crystallising Compound (I) from acetone and water. A typical ratio of acetone to water that is suitable for this process is between 5:1 and 200:1 e.g. around 10:1. Alternatively, form B may be obtained by crystallising Compound (I) from acetone alone. Detailed preparations of Compound (I) as the anhydrous free base in solid crystalline polymorphic forms A and B are provided in Examples 1 and 3 of the Experimental Section, respectively.

In a further aspect of the invention, the solid state properties of Compound (I) may be improved by further slurrying or recrystallization steps to produce, for example, material with improved morphology and/or containing a reduced level of residual solvent. For example, residual solvent may be removed from Compound (I) as the anhydrous free base in solid, crystalline, polymorphic form B by slurrying Compound (I) in polymorphic form B, in water, or alternatively by further recrystallization from acetone. A detailed description of an exemplary slurrying procedure is provided in Example 3a of the Experimental Section.

In one embodiment, there is provided solid, crystalline polymorphic form A of Compound (I) as the anhydrous free base having an XRPD pattern substantially as shown in FIG. 1. The method of obtaining the XRPD data is described in Analytical Methods and the data discussed in Example 5.

Thus, there is provided Compound (I) as the anhydrous free base in solid, crystalline, polymorphic form A having an XRPD pattern with at least one (for example one, two, three, four, five, six, seven, eight, nine, ten, eleven, twelve, thirteen, fourteen, fifteen or all sixteen) peak(s) at 7.8, 8.7, 10.3, 11.2, 12.4, 15.2, 16.2, 17.5, 19.7, 20.8, 22.6, 23.1, 24.6, 25.5, 26.7, 27.4 (±0.2 degrees, 2-theta values), these peaks being characteristic of the solid, crystalline, polymorphic form A. The peaks at 10.3, 15.2, 17.5, 23.1, 24.6, 26.7 and 27.4 are particularly characteristic for the solid, crystalline, polymorphic form A and therefore it is preferable that at least one (for example one, two, three, four, five, six or all seven) of these peaks is observable in the XRPD pattern.

Figure 2:
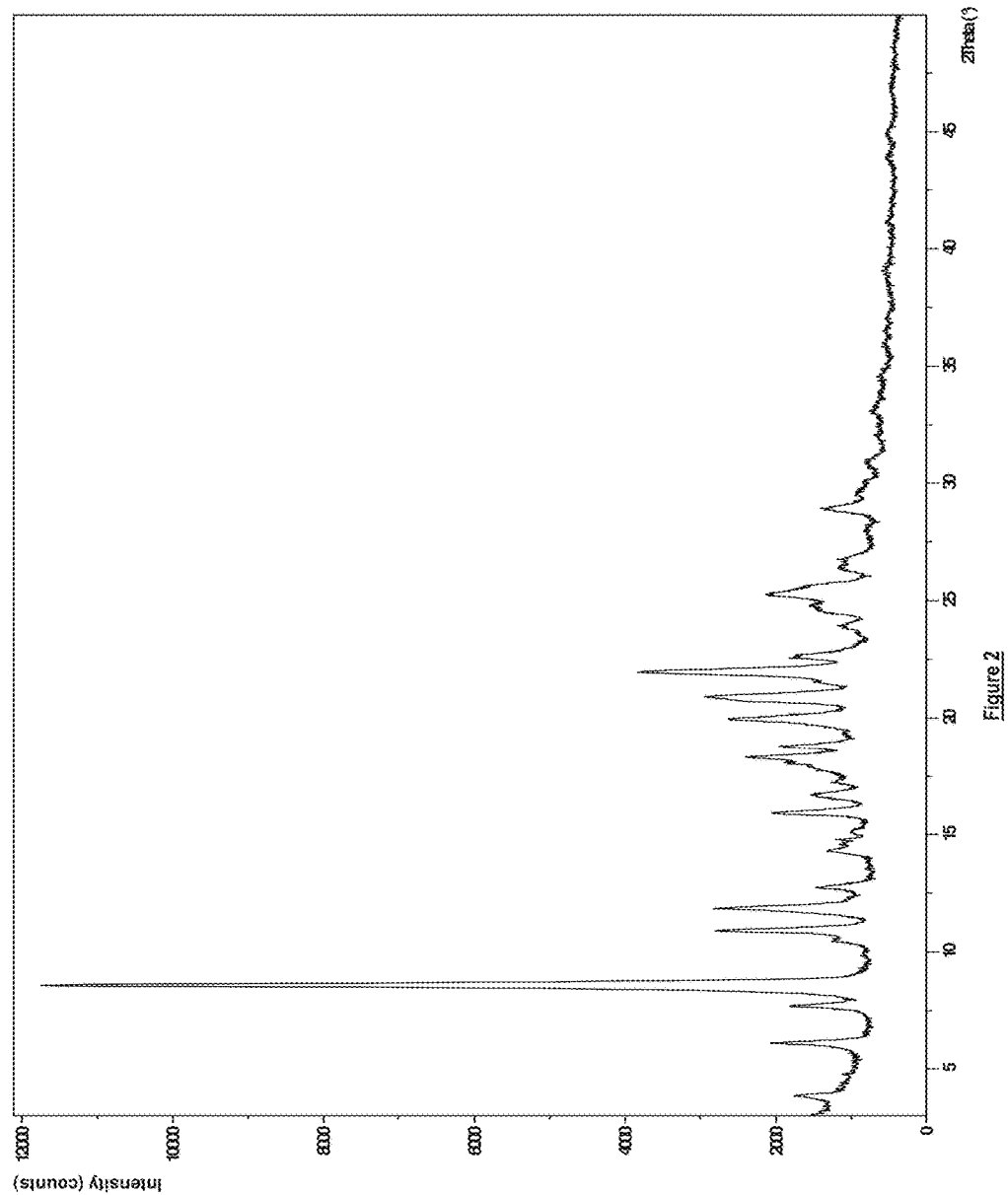
FIG. 2 displays an XRPD pattern acquired from a sample of Compound (I) as the anhydrous free base in solid crystalline polymorphic form B, post micronization.

In another embodiment, there is provided solid, crystalline, polymorphic form B of Compound (I) as the anhydrous free base (micronized) having an XRPD pattern substantially as shown in FIG. 2. The method of micronization is described in Example 4 and the method of obtaining the XRPD data is described in Analytical Methods and the data discussed in Example 5.

Thus, there is provided Compound (I) as the anhydrous free base in solid crystalline polymorphic form B (micronized) having an XRPD pattern with at least one (for example one, two, three, four, five, six, seven, eight, nine, ten, eleven, twelve, thirteen, fourteen, fifteen, sixteen, seventeen or all eighteen) peaks at 3.9, 6.1, 7.7, 8.6, 10.9, 11.8, 12.7, 14.3, 15.9, 16.7, 18.3, 18.7, 19.9, 20.9, 22.0, 22.6, 25.2, 28.9 (±0.2 degrees, 2-theta values), these peaks being characteristic of the solid crystalline polymorphic form B. The peaks at 3.9, 6.1, 11.8, 14.3, 16.7, 18.3, 18.7 and 28.9 are particularly characteristic for the solid, crystalline, polymorphic form B and therefore it is preferable that at least one (for example one, two, three, four, five, six, seven or all eight) of these peaks is observable in the XRPD pattern.

The melting points of Compound (I) as the anhydrous free base in solid, crystalline, polymorphic forms A and B were determined using differential scanning calorimetry as described in Example 6. Compound (I) as the anhydrous free base in solid, crystalline, polymorphic form A was found to have a melting point of 191.6° C., and Compound (I) as the anhydrous free base in solid, crystalline, polymorphic form B was found to have a melting point of 214° C. Polymorphic form B was also found to have a higher heat of fusion than polymorphic form A. As explained in Example 6, these results suggest that polymorphic form B is thermodynamically more stable than polymorphic form A.

The physical and chemical stabilities of Compound (I) as the anhydrous free base in solid, crystalline, polymorphic form B, were investigated, the results of which are disclosed herein.

In order to assess physical stability, Compound (I) as the anhydrous free base in solid, crystalline, polymorphic form B was micronized following the procedure described in Example 4, and samples of the resulting material were stored in open containers and subjected to different ambient temperatures and relative humidities. The physical properties and stabilities of the samples were investigated using TGA, DSC, DVS, IR spectroscopy and XRPD analysis. Full experimental procedures are provided in the General Procedures section and the results are summarised in Example 7 (Table 7). As discussed in Example 7, Compound (I) as the anhydrous free base in solid, crystalline, polymorphic form B (micronized) was found to have good physical stability. The same experimental procedures were also carried out using Compound (I) as the anhydrous free base in solid, crystalline, polymorphic form B in non-micronized form and the results were found to be substantially similar to those obtained for the micronized material i.e. Compound (I) as the anhydrous free base in solid, crystalline, polymorphic form B in both micronized and unmicronized forms was found to have good physical stability.

In order to assess chemical stability, Compound (I) as the anhydrous free base in solid, crystalline, polymorphic form B was micronized following the procedure described in Example 4. Micronized samples were stored in open containers and subjected to different ambient temperatures and relative humidities. The chemical stabilities of the samples were analysed by HPLC. The results are summarised in Example 8 (Table 8) where it is indicated that Compound (I) as the anhydrous free base in solid, crystalline, polymorphic form B, post microniastion was found to be chemically stable, although some sensitivity towards light was detected.

As a result of the solid state studies disclosed herein, it is concluded that Compound (I) as the anhydrous free base in solid, crystalline, polymorphic form B can be micronized and that the resulting material has good physical and chemical stability.

The compound of formula (I) is a p38 MAP kinase inhibitor (especially of the alpha subtype) and in one aspect the compound is useful in the treatment of inflammatory diseases, for example COPD and/or asthma.

Surprisingly, the compound exhibits a long duration of action and/or persistence of action in comparison to the previously disclosed p38 MAP kinase inhibitor BIRB796.

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compound of formula (I) is expected to be potent in vivo.

Typically, the prior art compounds developed to date have been intended for oral administration. This strategy involves optimizing compounds which achieve their duration of action by an appropriate pharmacokinetic profile, thereby ensuring that a sufficiently high drug concentration is established and maintained between doses to provide clinical benefit. The inevitable consequence of this approach is that all bodily tissues, and especially the liver and the gut, are exposed to supra-therapeutically active concentrations of the drug, whether or not they are adversely affected by the disease being treated.

An alternative strategy is to design treatment paradigms in which the drug is dosed directly to the inflamed organ (topical therapy). While this approach is not suitable for treating all chronic inflammatory diseases, it has been extensively exploited in lung diseases (asthma, COPD), skin conditions (atopic dermatitis and psoriasis), nasal diseases (allergic rhinitis) and gastrointestinal disorders (ulcerative colitis).

In topical therapy, efficacy can be achieved either by ensuring that the drug has a sustained duration of action and is retained in the relevant organ to minimize the risks of systemic toxicity or by producing a formulation which generates a "reservoir" of the active drug. which is available to sustain its desired effects. The first approach is exemplified by the anticholinergic drug tiotropium (Spiriva). This compound is administered topically to the lung as a treatment for COPD, and has an exceptionally high affinity for its target receptor, resulting in a very slow off rate and a consequent sustained duration of action.

In one aspect of the disclosure the compound of formula (I) is particularly suitable for topical delivery, such as topical delivery to the lungs, in particular for the treatment of respiratory disease, for example chronic respiratory diseases such as COPD and/or asthma.

In one embodiment the compound of formula (I) is suitable for sensitizing patients to treatment with a corticosteroid who have become refractory to such treatment regimens.

The compound of formula (I) may also be useful for the treatment of rheumatoid arthritis.

The compound of formula (I) may have antiviral properties, for example the ability to prevent infection of cells (such as respiratory epithelial cells) with a picornavirus, in particular a rhinovirus, influenza or respiratory syncytial virus.

Thus the compound is thought to be an antiviral agent, in particular suitable for the prevention, treatment or amelioration of picornavirus infections, such as rhinovirus infection, influenza or respiratory syncytial virus.

In one embodiment the compound of formula (I) is able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay as described in the Examples herein.

In one embodiment the compound of formula (I) is able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compound of formula (I) particularly suitable for use in the treatment and/or prophylaxis of exacerbations of inflamatory diseases, in particular viral exacerbations, in patients with one or more of the following chronic conditions such as congestive heart failure, COPD, asthma, diabetes, cancer and/or in immunosuppressed patients, for example post-organ transplant.

In particular, the compound of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, and COPD (including chronic bronchitis and emphysema).

The compound of formula (I) may also be useful in the treatment of one or more conditions which may be treated by topical or local therapy including allergic conjunctivitis, conjunctivitis, allergic dermatitis, contact dermatitis, psoriasis, ulcerative colitis, inflamed joints secondary to rheumatoid arthritis or to osteoarthritis.

It is also expected that the compound of formula (I) may be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

The compound of formula (I) may be useful in the treatment of eye diseases or disorders including allergic conjunctivitis, conjunctivitis, diabetic retinopathy, macular oedema (including wet macular oedema and dry macular oedema), post-operative cataract inflammation or, particularly, uveitis (including posterior, anterior and pan uveitis).

The compound of formula (I) may be useful in the treatment of gastrointestinal diseases or disorders including ulcerative colitis or Crohn's disease.

The compound of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

The present invention also provides a process for preparing such a pharmaceutical composition which comprising mixing the ingredients.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising Compound (I) of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoro methane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Nebulisers may be portable or non-portable Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of larger particle size e.g. an MMAD of 50 μm or more, e.g. 100 μm or more. An alternative topically acceptable diluent is mannitol. Examples of dry powder delivery systems include SPINHALER, DISKHALER, TURBOHALER, DISKUS and CLICKHALER. Further examples of dry powder inhaler systems include ECLIPSE, ROTAHALER, HANDIHALER, AEROLISER, CYCLOHALER, BREEZHALER/NEOHALER, FLOWCAPS, TWINCAPS, X-CAPS, TURBOSPIN, ELPENHALER, TURBUHALER, MIATHALER, TWISTHALER, NOVOLIZER, SKYEHALER, ORIEL dry powder inhaler, MICRODOSE, ACCUHALER, PULVINAL, EASYHALER, ULTRAHALER, TAI FUN, PULMOJET, OMNI HALER, GYROHALER, TAPER, CONIX, XCELOVAIR and PROHALER.

One aspect of the invention relates to a dry powder pharmaceutical formulation for inhalation comprising:

(i) Compound (I)

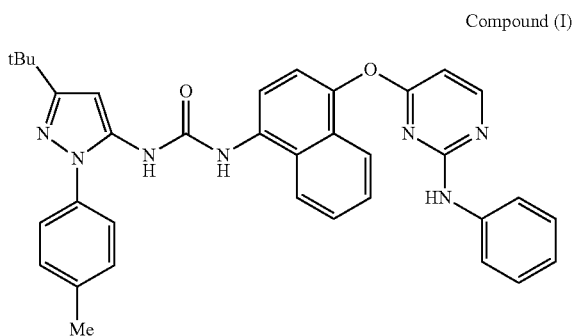 [SMILES: Cc1ccc(-n2nc(C(C)(C)C)cc2NC(=O)Nc2ccc(Oc3ccnc(Nc4ccccc4)n3)c3ccccc23)cc1]

Compound (I)

that is 1-(3-tert-butyl-1-p-tolyl-1H-pyrazol-5-yl)-3-(4-(2-(phenylamino)pyrimidin-4-yloxy)naphthalen-1-yl)urea or a pharmaceutically acceptable salt thereof, including all stereoisomers and tautomers thereof, in particulate form (e.g. solid crystalline Form B) as active ingredient;
(ii) particulate lactose as carrier; and
(iii) a particulate metal salt of stearic acid, such as magnesium stearate.

The invention also provides for an inhalation device comprising one or more doses of said formulation.

The compound of formula (I) has therapeutic activity. In a further aspect, the present invention provides a compound of the disclosure for use as a medicament. Thus, in a further aspect, the present invention provides a compound as described herein for use in the treatment of one or more of the above mentioned conditions.

In a further aspect, the present invention provides use of Compound (I) as described herein for the manufacture of a medicament for the treatment of one or more of the above mentioned conditions.

In a further aspect, the present invention provides a method of treatment of one or more of the above mentioned conditions which comprises administering to a subject an effective amount of Compound (I) of the disclosure or a pharmaceutical composition comprising the compound.

The word "treatment" is intended to embrace prophylaxis as well as therapeutic treatment.

Compound (I) of the invention may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline). Other suitable actives include anticholinergics, such as tiotropium and anti-viral agents such as, but not limited to, zanamivir or oseltamivir, for example as the phosphate. Other anti-viral agents include peramivir and laninamivir. Further possible combinations for treatment of respiratory disorders include combinations with steroids such as flunisolide, ciclesonide and triamcinolone; beta agonists such bambuterol, levalbuterol, clenbuterol, fenoterol, broxaterol, indacaterol, reproterol, procaterol and vilanterol; muscarinic antagonists, (e.g. ipratropium, tiotropium, oxitropium, glycopyrronium, glycopyrrolate, aclidinium, trospium) and leukotriene antagonists (e.g. zafirlukast, pranlukast, zileuton, montelukast). It will be understood that any of the aforementioned active ingredients may be employed in the form of a pharmaceutically acceptable salt.

In one embodiment the compound of formula (I) and the other active ingredient(s) are co-formulated in the same pharmaceutical formulation. In another embodiment the other active ingredient(s) are administered in one or more separate pharmaceutical formulations.

Hence, another aspect of the invention provides a combination product comprising:
(A) a compound of the present invention (i.e. a compound of formula (I) as defined above, or a pharmaceutically acceptable salt thereof); and
(B) another therapeutic agent,
wherein each of components (A) and (B) is formulated in admixture with a pharmaceutically-acceptable diluent or carrier.

In this aspect of the invention, the combination product may be either a single (combination) pharmaceutical formulation or a kit-of-parts.

Thus, this aspect of the invention encompasses a pharmaceutical formulation including a compound of the present invention and another therapeutic agent, in admixture with a pharmaceutically acceptable diluent or carrier (which formulation is hereinafter referred to as a "combined preparation").

It also encompasses a kit of parts comprising components:
(i) a pharmaceutical formulation including a compound of the present invention in admixture with a pharmaceutically acceptable diluent or carrier; and
(ii) a pharmaceutical formulation including another therapeutic agent, in admixture with a pharmaceutically-acceptable diluent or carrier,
which components (i) and (ii) are each provided in a form that is suitable for administration in conjunction with the other.

Component (i) of the kit of parts is thus component (A) above in admixture with a pharmaceutically acceptable diluent or carrier. Similarly, component (ii) is component (B) above in admixture with a pharmaceutically acceptable diluent or carrier.

The other therapeutic agent (i.e. component (B) above) may be, for example, any of the active ingredients mentioned above in connection with the treatment of respiratory disorders. The data reported hereinbelow in relation to the antiviral properties of the compound of formula (I) provides evidence that other antiviral therapies in combination with a compound of formula (I) would be useful in the treatment or prevention of virally-induced exacerbations (for example respiratory viral infections) suffered by patients with respiratory disease such as COPD and/or asthma and/or one or more of the indications listed above. Thus, in one aspect there is provided the use of Compound (I) in combination with an anti-viral therapy such as, but not limited to, zanamavir or oseltamivir (for example oseltamivir phosphate) in the treatment or prevention of respiratory viral infections suffered by patients with respiratory disease such as COPD and/or asthma.

The inventors also believe that other antiviral therapies in combination with Compound (I) would be useful in the treatment or prevention of virally induced exacerbations (for example respiratory viral infections) in patients with chronic conditions other than respiratory diseases, for example conditions such as congestive heart failure, diabetes, cancer, or conditions suffered by immunosuppressed patients, for example post-organ transplant. Thus, in a further aspect there is provided the use of a compound of the invention in combination with an anti-viral therapy, such as, but not limited to, zanamavir or oseltamivir (for example oseltamivir phosphate), in the treatment or prevention of respiratory viral infections in patients with chronic conditions such as congestive heart failure, diabetes, cancer, or in conditions suffered by immunosuppressed patients, for example post-organ transplant.

EXPERIMENTAL SECTION

Abbreviations used herein are defined below (Table 1). Any abbreviations not defined are intended to convey their generally accepted meaning.

TABLE 1

| Abbreviations | |
|---|---|
| AcOH | glacial acetic acid |
| Aq | aqueous |
| ATP | adenosine-5'-triphosphate |
| BALF | bronchoalveolae lavage fluid |
| BEGM | bronchial epithelial cell growth media |
| br | broad |
| BSA | bovine serum albumin |
| CatCart ® | catalytic cartridge |
| CDI | 1,1-carbonyl-diimidazole |
| COPD | chronic obstructive pulmonary disease |
| CXCL1 | chemokine (C-X-C motif) ligand 1 |
| d | doublet |
| DCM | dichloromethane |
| DMSO | dimethyl sulfoxide |
| DSC | differential scanning calorimetry |
| d-U937 cells | PMA differentiated U-937 cells |
| DVS | dynamic vapour sorption |
| (ES+) | electrospray ionization, positive mode |
| Et | ethyl |
| EtOAc | ethyl acetate |
| FCS | foetal calf serum |
| FRET | fluorescence resonance energy transfer |
| GSK3α | glycogen synthase kinase 3α |
| HBEC | primary human bronchial epithelial cells |
| hr | hour(s) |
| HRP | horseradish peroxidise |
| HRV | human rhinovirus |
| ICAM-1 | inter-cellular adhesion molecule 1 |
| IR | infrared |
| JNK | c-Jun N-terminal kinase |
| KC | keratinocyte chemoattractant |
| Kd | dissociation constant |
| LPS | Lipopolysaccharide |
| (M + H)+ | protonated molecular ion |
| MAPK | mitogen protein activated protein kinase |
| MAPKAP-K2 | mitogen-activated protein kinase-activated protein kinase-2 |
| Me | methyl |
| MeCN | acetonitrile |
| MeOH | methanol |
| MHz | megahertz |
| min | minute(s) |
| MIP1α | macrophage inflammatory protein 1 alpha |
| MMAD | mass median aerodynamic diameter |
| MOI | multiplicity of infection |
| m.p. | melting point |
| MTT | 3-(4,5-dimethylthiazol-2-yl)-2,5-diphenyltetrazolium bromide |
| m/z: | mass-to-charge ratio |
| NMR | nuclear magnetic resonance (spectroscopy) |
| PBMC | peripheral blood mononuclear cell |
| PBS | phosphate buffered saline |
| Ph | phenyl |
| PHA | phytohaemagglutinin |
| PMA | phorbol myristate acetate |
| pTSA | 4-methylbenzenesulfonic acid |
| q | quartet |
| RT | room temperature |
| RP HPLC | reverse phase high performance liquid chromatography |
| RSV | respiratory syncytical virus |
| s | singlet |
| sat | saturated |

TABLE 1-continued

| Abbreviations | |
|---|---|
| SCX | solid supported cation exchange (resin) |
| SDS | sodium dodecyl sulphate |
| $S_NAr$ | nucleophilic aromatic substitution |
| t | triplet |
| $TCID_{50}$ | 50% tissue culture infectious dose |
| TGA | thermogravimetric analysis |
| THF | tetrahydrofuran |
| TNFα | tumor necrosis factor alpha |
| XRPD | X-ray powder diffraction |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated. Column chromatography was performed on pre-packed silica (230-400 mesh, 40-63 μm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography:

Agilent Scalar column C18, 5 μm (21.2×50 mm), flow rate 28 mL min$^{-1}$ eluting with a $H_2O$-MeCN gradient containing 0.1% v/v formic acid over 10 min using UV detection at 215 and 254 nm. Gradient information: 0.0-0.5 min; 95% $H_2O$-5% MeCN; 0.5-7.0 min; ramped from 95% $H_2O$-5% MeCN to 5% $H_2O$-95% MeCN; 7.0-7.9 min; held at 5% $H_2O$-95% MeCN; 7.9-8.0 min; returned to 95% $H_2O$-5% MeCN; 8.0-10.0 min; held at 95% $H_2O$-5% MeCN.

Analytical Methods

Reverse Phase High Performance Liquid Chromatography:

(Method 1): Agilent Scalar column C18, 5 μm (4.6×50 mm) or Waters XBridge C18, 5 μm (4.6×50 mm) flow rate 2.5 mL min$^{-1}$ eluting with a $H_2O$-MeCN gradient containing either 0.1% v/v formic acid (Method 1 acidic) or $NH_3$ (Method 1 basic) over 7 min employing UV detection at 215 and 254 nm. Gradient information: 0.0-0.1 min, 95% $H_2O$-5% MeCN; 0.1-5.0 min, ramped from 95% $H_2O$-5% MeCN to 5% $H_2O$-95% MeCN; 5.0-5.5 min, held at 5% $H_2O$-95% MeCN; 5.5-5.6 min, held at 5% $H_2O$-95% MeCN, flow rate increased to 3.5 mL min$^{-1}$; 5.6-6.6 min, held at 5% $H_2O$-95% MeCN, flow rate 3.5 mL min$^{-1}$; 6.6-6.75 min, returned to 95% $H_2O$-5% MeCN, flow rate 3.5 mL min$^{-1}$; 6.75-6.9 min, held at 95% $H_2O$-5% MeCN, flow rate 3.5 mL·min$^{-1}$; 6.9-7.0 min, held at 95% $H_2O$-5% MeCN, flow rate reduced to 2.5 mL min$^{-1}$.

Reverse Phase High Performance Liquid Chromatography:

(Method 2): Agilent Extend C18 column, 1.8 μm (4.6×30 mm) at 40° C.; flow rate 2.5-4.5 mL min$^{-1}$ eluting with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01 3.50 min, held at 5% $H_2O$-95% MeCN; 3.50-3.60 min, returned to 95% $H_2O$-5% MeCN, flow rate reduced to 3.50 mL min$^{-1}$;

3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy:

Spectra were acquired on a Bruker Avance III spectrometer at 400 MHz using residual undeuterated solvent as reference.

Dynamic Vapour Sorption:

Plots were obtained using a Surface Measurement Systems dynamic vapor sorption model DVS-1 using about 10 mg of the sample. The weight change was recorded with respect to atmospheric humidity at 25° C. and was determined using the following parameters: drying: 60 min under dry nitrogen; equilibrium: 60 min/step; data interval: 0.05% or 2.0 min. The relative humidity [RH %] measurement points were as follows:

first set: 5, 10, 20, 30, 40, 50, 60, 70, 80, 90, 95, 90, 80, 70, 60, 50, 40, 30, 20, 10, 5 second set: 10, 20, 30, 40, 50, 60, 70, 80, 90, 95, 90, 80, 70, 60, 50, 40, 30, 20, 10, 5, 0.

X-Ray Powder Diffraction:

Patterns were obtained on a PANalytical (Philips) X'PertPRO MPD diffractometer equipped with a Cu LFF X-ray tube (45 kV; 40 mA; Bragg-Brentano; spinner stage) and were acquired using Cu Kα radiation under the following measurement conditions: scan mode: continuous; scan range: 3 to 50° 2θ; step size: 0.02°/step; counting time: 30 sec/step; spinner revolution time: 1 sec; incident beam path: program. divergence slit: 15 mm; Soller slit: 0.04 rad; beam mask: 15 mm; anti scatter slit: 1°; beam knife: +; Diffracted beam path: long anti scatter shield: +; Soller slit: 0.04 rad; Ni filter: +; detector: X'Celerator. Samples were prepared by spreading on a zero background sample holder.

Infrared Spectroscopy:

Micro attenuated total reflectance (microATR) was used and the sample was analyzed using a suitable microATR accessory and the following measurement conditions: apparatus: Thermo Nexus 670 FTIR spectrometer; number of scans: 32; resolution: 1 cm$^{-1}$; wavelength range: 4000 to 400 cm$^{-1}$; detector: DIGS with KBr windows; beamsplitter: Ge on KBr; micro ATR accessory: Harrick Split Pea with Si crystal.

Differential Scanning Calorimetry:

Data were collected on a TA-Instruments Q1000 MTDSC equipped with RCS cooling unit. Typically 3 mg of each compound, in a standard aluminium TA-Instrument sample pan, was heated at 10° C./min from 25 C to 300° C. A nitrogen purge at 50 mL/min was maintained over the sample.

Thermogravimetric Analysis:

Data were collected on a TA-Instruments Q500 thermogravimeter Typically 10 mg of each sample was transferred into a pre-weighed aluminium pan and was heated at 20° C./min from ambient temperature to 300° C. or <80[(w/w) %] unless otherwise stated.

Chemical Stability by HPLC:

Analyses were carried out on a Waters Xbridge C$_{18}$ column (3.0×150 mm; 3.5 μm) using the following operating conditions: column temperature: 40° C.; sample temperature: 5° C.; flow rate: 0.45 mL/min; injection volume: 7 μL; UV detection at 260 nm; mobile phase composition comprised of Phase A: 10 mM ammonium acetate+0.1%, v/v trifluoroacetic acid in water and Phase B: acetonitrile, using the gradient defined by the parameters below (Table 2).

TABLE 2

Gradient Conditions for Chemical Stability Studies by HPLC.

| Eluent | % Composition at Run Time (min) | | | | |
|---|---|---|---|---|---|
| | 0 | 20 | 25 | 26 | 32 |
| Phase A | 70 | 0 | 0 | 70 | 70 |
| PhaseB | 30 | 100 | 100 | 30 | 30 |

Experimental Methods for Biological Testing

Enzyme Inhibition Assays

The kinase enzyme binding activities of compounds disclosed herein were determined using a proprietary assay which measures active site-directed competition binding to an immobilized ligand (Fabian, M. A. et al., Nature Biotechnol., 2005, 23:329-336). These assays were conducted by DiscoverX (formerly Ambit; San Diego, Calif.). The Kd value (Dissociation constant value) was calculated as the index of affinity of the compounds to each kinase.

Enzyme Inhibition Assays

The enzyme inhibitory activities of compounds disclosed herein were determined by FRET using synthetic peptides labelled with both donor and acceptor fluorophores (Z-LYTE, Invitrogen Ltd., Paisley, UK).

p38 MAPKα Enzyme Inhibition

The inhibitory activities of test compounds against the p38 MAPKα isoform (MAPK14: Invitrogen), were evaluated indirectly by determining the level of activation/phosphorylation of the down-stream molecule, MAPKAP-K2. The p38 MAPKα protein (80 ng/mL, 2.5 μL) was mixed with the test compound (2.5 μL of either 4 μg/mL, 0.4 μg/mL, 0.04 μg/mL or 0.004 μg/mL) for 2 hr at RT. The mix solution (2.5 μL) of the p38a inactive target MAPKAP-K2 (Invitrogen, 600 ng/mL) and FRET peptide (8 μM; a phosphorylation target for MAPKAP-K2) was then added and the kinase reaction was initiated by adding ATP (40 μM, 2.5 μL). The mixture was incubated for 1 hr at RT. Development reagent (protease, 5 μL) was added for 1 hr prior to detection in a fluorescence microplate reader (Varioskan® Flash, ThermoFisher Scientific).

p38 MAPKγ Enzyme Inhibition

The inhibitory activities of compounds of the invention against p38MAPKγ (MAPK12: Invitrogen), were evaluated in a similar fashion to that described hereinabove. The enzyme (800 ng/mL, 2.5 μL) was incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) was then added to the enzymes/compound mixtures and incubated for 1 hr. Development reagent (protease, 5 μL) was added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), were evaluated in a similar fashion to that described hereinabove. The relevant enzyme (3000 ng/mL or 2000 ng/mL respectively, 2.5 μL) was incubated with the test compound (either 4 μg/mL, 0.4 μg/mL, 0.04 μg/mL, or 0.004 μg/mL, 2.5 μL each) for 2 hr at RT. The FRET peptides (8 μM, 2.5 μL), and appropriate ATP solutions (2.5 μL, 800 μM for c-Src, and 60 μM ATP for Syk) were then added to the enzyme/compound mixtures and incubated for 1 hr. Development reagent (protease, 5 µL) was added for 1 hr prior to detection in a fluorescence microplate reader (Varioskan® Flash, ThermoFisher Scientific).

GSK 3α Enzyme Inhibition

The inhibitory activities of test compounds against the GSK 3α enzyme isoform (Invitrogen), were evaluated by determining the level of activation/phosphorylation of the target peptide. The GSK3-α protein (500 ng/mL, 2.5 µL) was mixed with the test compound (2.5 µL at either 4 µg/mL, 0.4 µg/mL, 0.04 µg/mL, or 0.004 µg/mL) for 2 hr at RT. The FRET peptide (8 µM, 2.5 µL), which is a phosphorylation target for GSK3α, and ATP (40 µM, 2.5 µL) were then added to the enzyme/compound mixture and the resulting mixture incubated for 1 hr. Development reagent (protease, 5 µL) was added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction were calculated using the ratio of coumarin emission (donor) over fluorescein emission (acceptor), for which low ratios indicate high phosphorylation and high ratios indicate low phosphorylation levels. The percentage inhibition of each reaction was calculated relative to non-inhibited control and the 50% inhibitory concentration ($IC_{50}$ value) was then calculated from the concentration-response curve.

Cellular Assays

LPS-Induced TNFα/IL-8 Release in d-U937 Cells

U937 cells, a human monocytic cell line, were differentiated into macrophage-type cells by incubation with PMA (100 ng/mL) for 48 to 72 hr. Cells were pre-incubated with final concentrations of test compound for 2 hr and were then stimulated with LPS (0.1 µg/mL; from E. Coli: 0111:64, Sigma) for 4 hr. The supernatant was collected for determination of TNFα and IL-8 concentrations by sandwich ELISA (Duo-set, R&D systems). The inhibition of TNFα production was calculated as a percentage of that achieved by 10 µg/mL of BIRB796 at each concentration of test compound by comparison against vehicle control. The relative 50% effective concentration ($REC_{50}$) was determined from the resultant concentration-response curve. The inhibition of IL-8 production was calculated at each concentration of test compound by comparison with vehicle control. The 50% inhibitory concentration ($IC_{50}$) was determined from the resultant concentration-response curve.

LPS-Induced TNFα Release in THP-1 Cells

THP-1 cells, a human monocytic cell line, were stimulated with 3 µg/mL of LPS (from E. Coli; 0111:64, Sigma) for 4 hr and the supernatant collected for determination of the TNFα concentration by sandwich ELISA (Duo-set, R&D systems). The inhibition of TNFα production was calculated at each concentration by comparison with vehicle control. The 50% inhibitory concentration ($IC_{50}$) was determined from the resultant concentration-response curve.

Poly I:C-Induced ICAM-1 Expression in BEAS2B Cells

Poly I:C was used in these studies as a simple, RNA virus mimic. Poly I:C-Oligofectamine mixture (1 µg/mL Poly I:C, ±2% Oligofectamine, 25 µL; Invivogen Ltd., San Diego, Calif., and Invitrogen, Carlsbad, Calif., respectively) was transfected into BEAS2B cells (human bronchial epithelial cells, ATCC). Cells were pre-incubated with final concentrations of test compounds for 2 hr and the level of ICAM-1 expression on the cell surface was determined by cell-based ELISA. At a time point 18 hr after poly I:C transfection, cells were fixed with 4% formaldehyde in PBS (100 µL) and then endogenous peroxidase was quenched by the addition of washing buffer (100 µL, 0.05% Tween in PBS: PBS-Tween) containing 0.1% sodium azide and 1% hydrogen peroxide. Cells were washed with wash-buffer (3×200 µL). and after blocking the wells with 5% milk in PBS-Tween (100 µL) for 1 hr, the cells were incubated with anti-human ICAM-1 antibody (50 µL; Cell Signaling Technology, Danvers, Mass.) in 1% BSA PBS overnight at 4° C.

The cells were washed with PBS-Tween (3×200 µL) and incubated with the secondary antibody (100 µL; HRP-conjugated anti-rabbit IgG, Dako Ltd., Glostrup, Denmark). The cells were then incubated with of substrate (50 µL) for 2-20 min, followed by the addition of stop solution (50 µL, 1N $H_2SO_4$). The ICAM-1 signal was detected by reading and reading the absorbance at 450 nm against a reference wavelength of 655 nm using a spectrophotometer. The cells were then washed with PBS-Tween (3×200 µL) and total cell numbers in each well were determined by reading absorbance at 595 nm after Crystal Violet staining (50 µL of a 2% solution in PBS) and elution by 1% SDS solution (100 µL) in distilled water. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

Cell Mitosis Assay

Peripheral blood mononucleocytes (PBMCs) from healthy subjects were separated from whole blood (Quintiles, London, UK) using a density gradient (Histopaque-1077, Sigma-Aldrich, Poole, UK). The PBMCs (3 million cells per sample) were subsequently treated with 2% PHA (Sigma-Aldrich, Poole, UK) for 48 hr, followed by a 20 hr exposure to varying concentrations of test compounds. At 2 hr before collection, PBMCs were treated with demecolcine (0.1 µg/mL; Invitrogen, Paisley, UK,) to arrest cells in metaphase. To observe mitotic cells, PBMCs were permeabilised and fixed by adding Intraprep (50 µL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK,) as previously described (Muehlbauer P. A. and Schuler M. J., *Mutation Research,* 2003, 537:117-130). Fluorescence was observed using an ATTUNE flow cytometer (Invitrogen, Paisley, UK), gating for lymphocytes. The percentage inhibition of mitosis was calculated for each treatment relative to vehicle (0.5% DMSO) treatment.

Rhinovirus-Induced IL-8 Release and ICAM-1 Expression

Human rhinovirus RV16 was obtained from the American Type Culture Collection (Manassas, Va.). Viral stocks were generated by infecting Hela cells with HRV until 80% of the cells were cytopathic.

BEAS2B cells were infected with HRV at an MOI of 5 and incubated for 2 hr at 33° C. with gentle shaking for to promote absorption. The cells were then washed with PBS, fresh media added and the cells were incubated for a further 72 hr. The supernatant was collected for assay of IL-8 concentrations using a Duoset ELISA development kit (R&D systems, Minneapolis, Minn.).

The level of cell surface ICAM-1 expression was determined by cell-based ELISA. At 72 hr after infection, cells were fixed with 4% formaldehyde in PBS. After quenching endogenous peroxidase by adding 0.1% sodium azide and 1% hydrogen peroxide, wells were washed with wash-buffer (0.05% Tween in PBS: PBS-Tween). After blocking well with 5% milk in PBS-Tween for 1 hr, the cells were incubated with anti-human ICAM-1 antibody in 5% BSA PBS-Tween (1:500) overnight. Wells were washed with PBS-Tween and incubated with the secondary antibody (HRP-conjugated anti-rabbit IgG, Dako Ltd.). The ICAM-1 signal was detected by adding substrate and reading at 450 nm with a reference wavelength of 655 nm using a spectrophotometer. The wells were then washed with PBS-Tween and total cell numbers in each well were determined by reading absorbance at 595 nm after Crystal Violet staining and elution by 1% SDS solution. The measured $OD_{450\text{-}655}$ readings were corrected for cell number by dividing with the $OD_{595}$ reading in each well. Compounds were added 2 hr before HRV infection and 2 hr after infection when non-infected HRV was washed out.

Assessment of HRV16 Induced CPE in MRC5 Cells

MRC-5 cells were infected with HRV16 at an MOI of 1 in DMEM containing 5% FCS and 1.5 mM $MgCl_2$, followed by incubation for 1 hr at 33° C. to promote adsorption. The supernatants were aspirated, and then fresh media added followed by incubation for 4 days. Where appropriate, cells were pre-incubated with compound or DMSO for 2 hr, and the compounds and DMSO added again after washout of the virus.

Supernatants were aspirated and incubated with methylene blue solution (100 µL, 2% formaldehyde, 10% methanol and 0.175% Methylene Blue) for 2 hr at RT. After washing, 1% SDS in distilled water (100 µL) was added to each well, and the plates were shaken lightly for 1-2 hr prior to reading the absorbance at 660 nm. The percentage inhibition for each well was calculated. The $IC_{50}$ value was calculated from the concentration-response curve generated by the serial dilutions of the test compounds.

In Vitro RSV Virus Load in Primary Bronchial Epithelial Cells.

Normal human bronchial epithelial cells (NHBEC) grown in 96 well plates were infected with RSV A2 (Strain A2, HPA, Salisbury, UK) at an MOI of 0.001 in the LHC8 Media:RPMI-1640 (50:50) containing 15 mM magnesium chloride and incubated for 1 hr at 37° C. for adsorption. The cells were then washed with PBS (3×200 µL), fresh media (200 µL) was added and incubation continued for 4 days. Where appropriate, cells were pre-incubated with the compound or DMSO for 2 hr, and then added again after washout of the virus.

The cells were fixed with 4% formaldehyde in PBS solution (50 µL) for 20 min, washed with washing buffer (3×200 µL; PBS including 0.5% BSA and 0.05% Tween-20) and incubated with blocking solution (5% condensed milk in PBS) for 1 hr. Cells were then washed with washing buffer (3×200 µL) and incubated for 1 hr at RT with anti-RSV (2F7) F-fusion protein antibody (40 µL; mouse monoclonal, lot 798760, Cat. No. ab43812, Abcam) in 5% BSA in PBS-tween). After washing, cells were incubated with an HRP-conjugated secondary antibody solution (50 µL) in 5% BSA in PBS-Tween (lot 00053170, Cat. No. P0447, Dako) and then TMB substrate (50 µL; substrate reagent pack, lot 269472, Cat. No. DY999, R&D Systems, Inc.) was added. This reaction was stopped by the addition of 2N $H_2SO_4$ (50 µL) and the resultant signal was determined colorimetrically (OD: 450 nm with a reference wavelength of 655 nm) in a microplate reader (Varioskan® Flash, ThermoFisher Scientific).

Cells were then washed and a 2.5% crystal violet solution (50 µL; lot 8656, Cat. No. PL7000, Pro-Lab Diagnostics) was applied for 30 min. After washing with washing buffer, 1% SDS in distilled water (100 µL) was added to each well, and plates were shaken lightly on the shaker for 1 hr prior to reading the absorbance at 595 nm. The measured $OD_{450\text{-}655}$ readings were corrected to the cell number by dividing the $OD_{450\text{-}655}$ by the $OD_{595}$ readings. The percentage inhibition for each well was calculated and the $IC_{50}$ value was calculated from the concentration-response curve generated from the serial dilutions of compound.

The Effect of Test Compounds on Cell Viability: MTT Assay

Differentiated U937 cells were pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant was replaced with new media (200 µL) and MTT stock solution (10 µL, 5 mg/mL) was added to each well. After incubation for 1 hr the media were removed, DMSO (200 µL) was added to each well and the plates were shaken lightly for 1 hr prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

Cytokine Production in Sputum Macrophages from COPD.

Patients with COPD were inhaled with a nebulised solution of 3% (w/v) hypertonic saline using an ultrasonic nebuliser (Devilbiss, Carthage, Mo.) with tidal breathing for 5 min. This procedure was repeated a maximum of three times until enough sputum was obtained. The sputum samples were homogenized and mixed vigorously using a vortex mixer in 0.02% v/v dithiothreitol (DTT) solution. The samples were re-suspended in PBS (40 mL) followed by centrifugation at 1500 rpm at 4° C. for 10 min to obtain sputum cell pellets. The pellets were washed twice with PBS (40 mL). The sputum cells were then re-suspended in macrophage serum-free medium (macrophage-SFM, Life technologies, Paisley, UK; to achieve $2\times10^6$/well in a 24 well plate) containing 20 U/mL penicillin, 0.02 mg/mL streptomycin and 5 µg/mL amphotericin B and seeded on high bound 96-well plate, followed by incubation for 2 hr at 37° C. and at 5% $CO_2$ to allow the macrophages to attach to the bottom of the plate. The cells on the plate were washed with fresh macrophage-SFM (200 µL/well) to remove neutrophils and other contaminated cells. The adherent cells (mainly sputum macrophages) on the plate were used for further analysis. Sputum induction and isolation were conducted in Quintiles Drug Research Unit at Guys Hospital and ethics approval and written informed consent was obtained by Quintiles.

Where appropriate, 1 µL of a solution containing either the test compound or reference article at the stated concentrations or alternatively 1 µL of DMSO as the vehicle control was added to each well (200 µL in media) and the cells were incubated for 2 hr. The cells were stimulated with LPS solution (50 µL, final concentration: 1 µg/mL) and incubated for 4 hr at 37° C. and 5% $CO_2$. The supernatant was then collected and kept at −80° C. Millipore's luminex kits were used to measure the four analytes. After thawing the supernatant, the magnetic antibody beads were multiplexed and incubated in a 96-well plate with standard, background solution or the appropriate volume of sample overnight with shaking at 4° C. After washing twice with 200 µL of wash buffer provided by the kit per well using a magnetic plate washer, the beads were incubated for 1 hr at RT with 25 µL of the biotin conjugated antibody solution provided by the kit with shaking. Streptavidin solution was added for 30 min with shaking at RT. After washing with 200 uL wash buffer per well, the beads were resuspended in sheath fluid (150 µL) and analyzed immediately. The level of each analyte in the supernatant was calculated using Xcel Fit software with a 4 or 5-parameter equation using each standard curve. The inhibitions of each cytokine production were calculated at each concentration by comparison with vehicle control. The $IC_{50}$ values were determined from concentration-inhibition curves using XL-Fit (idbs, Guildford, UK)

Cytokine Production in Primary Bronchial Epithelial Cells from COPD.

Primary airway epithelial cells obtained from patients with COPD were purchased from Asterand (Royston, UK), and maintained in bronchial epithelial cell growth media that was prepared by mixing together LHC8 (Invitrogen) (500 mL), with LHC9 (Invitrogen) (500 mL) and 3 µL of retinoic acid solution (5 mg/mL in neat DMSO. The media was removed by aspiration and fresh BEGM (200 µL) was added to each well. Where appropriate, 1 µL of a solution of the test compound at the state concentrations or 1 µL of DMSO as the vehicle control was added and the cells were incubated for 2 hr. The cells were stimulated with TNFα (50 µL; final concentration 50 ng/mL) and then incubated for 4 hr at 37° C. and 5% $CO_2$. The supernatant was then collected and kept at −20° C.

The levels of IL-6 and IL-8 were determined by ELISA using R&D Systems' Human IL-6 and IL-8 Duoset® Elisa Kits. The inhibition of IL-6 and IL-8 production was calculated at each concentration by comparison with vehicle control. The 50% inhibitory concentrations (ICA were determined from the resultant concentration-response curves using XL-Fit (idbs, Guildford, UK).

In Vivo Screening: Pharmacodynamics and Anti-Inflammatory Activity

LPS-Induced Neutrophil Accumulation in Mice

Non-fasted Balb/c mice were dosed by the intra tracheal route with either vehicle, or the test substance at the indicated times (within the range 2-8 hr) before stimulation of the inflammatory response by application of an LPS challenge. At T=0, mice were placed into an exposure chamber and exposed to LPS (7.0 mL, 0.5 mg/mL solution in PBS) for 30 min). After a further 8 hr the animals were anesthetized, their tracheas cannulated and BALF extracted by infusing and then withdrawing from their lungs 1.0 mL of PBS via the tracheal catheter. Total and differential white cell counts in the BALF samples were measured using a Neubaur haemocytometer. Cytospin smears of the BALF samples were prepared by centrifugation at 200 rpm for 5 min at RT and stained using a DiffQuik stain system (Dade Behring). Cells were counted using oil immersion microscopy. Data for neutrophil numbers in BAL are shown as mean±S.E.M. (standard error of the mean). The percentage inhibition of neutrophil accumulation was calculated for each treatment relative to vehicle treatment.

Cigarette Smoke Model

NJ mice (males, 5 weeks old) were exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances were administered intra-nasally (35 µL of solution in 50% DMSO/PBS) once daily for 3 days after the final cigarette smoke exposure. At 12 hr after the last dosing, each of the animals was anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil). BALF was centrifuged and the supernatant was collected. The level of keratinocyte chemoattractant (KC; CXCL1) in BALF was quantitated using a Quentikine® mouse KC ELISA kit (R&D systems, Inc., Minneapolis, Minn., USA).

Example 1—Preparation of Compound (I)

The following intermediates used to prepare Compound (I) of the invention have been previously described and were prepared using the procedures contained in the references cited below (Table 3).

TABLE 3

Previously Described Intermediates.

| Intermediate | Structure | Name, LCMS Data and Reference |
|---|---|---|
| A | [structure: 3-tert-butyl-1-p-tolyl-1H-pyrazol-5-amine] | 3-tert-butyl-1-p-tolyl-1H-pyrazol-5-amine. $R^t$ 2.46 min (Method 1 basic); m/z 230 (M + H)$^+$, (ES$^+$). Cirillo, P. F. et al., WO 2000/43384, 27 Jul. 2000. |
| B | [structure: 4-((2-chloropyrimidin-4-yl)oxy)naphthalen-1-amine] | 4-((2-chloropyrimidin-4-yl)oxy)naphthalen-1-amine. $R^t$ 1.80 min (Method 2); m/z 272/274 (M + H)$^+$, (ES$^+$). Cirillo, P. F. et al., WO 2002/92576, 21 Nov. 2000. |

Intermediate C: 4-((4-Aminonaphthalen-1-yl)oxy)-N-phenylpyrimidin-2-amine

Intermediate B $\xrightarrow{\text{Aniline}}$ pTSA

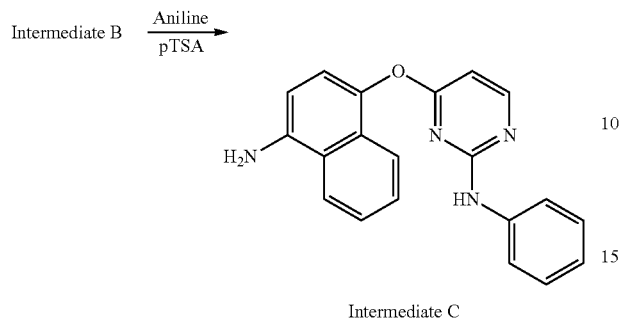

Intermediate C

To a nitrogen purged solution of mixture of Intermediate B (50.0 g, 184 mmol) and aniline (42.0 mL, 460 mmol) in THF (200 mL) was added pTSA (17.5 g, 92.0 mmol) in a single portion. The reaction mixture was heated to 70° C. for 1.5 hr during which time which a precipitate formed. The mixture was cooled to RT and diluted with THF (200 mL). The precipitate was collected by filtration, washed with THF (2×100 mL) and then suspended in a heterogeneous mixture of DCM (600 mL) and aq. NaOH (2M, 200 mL) and stirred vigorously for 1 hr, during which time the suspended solids dissolved. The layers were separated and the aq layer was extracted with DCM (200 mL). The DCM extracts were combined, dried and evaporated in vacuo. The residue was triturated with ether (150 mL) and the resulting solid was washed with ether (2×50 mL) to afford Intermediate C as an off white solid (26 g, 43%); $R^t$ 1.95 min (Method 2); m/z 329 (M+H)$^+$ (ES$^+$).

Compound (I): 1-(3-(tert-Butyl)-1-(p-tolyl)-1H-pyrazol-5-yl)-3-(4-((2-(phenylamino) pyrimidin-4-yl)oxy)naphthalen-1-yl)urea Intermediate A $\xrightarrow{\text{1. PhOC(O)Cl}}_{\text{2. Intermediate C}}$

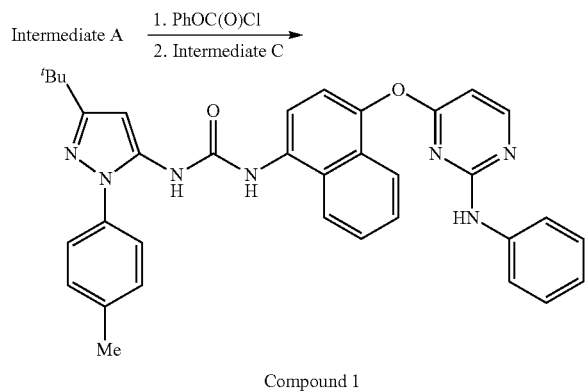

Compound 1

A heterogeneous mixture of a solution of Na$_2$CO$_3$ (3.84 g, 36 mmol) in water (42 mL) and Intermediate A (10.5 g, 45.7 mmol) in isopropyl acetate (130 mL, 1.082 mol) was stirred vigorously at RT for 5 min and was then treated with phenyl carbonochloridate (5.77 mL, 45.7 mmol). Stirring of the mixture was continued for a further 4 hr after which the layers were separated. The organic phase was added to a solution of Intermediate C (10.0 g, 30.5 mmol) and triethylamine (423 μL, 3.05 mmol) in isopropyl acetate (60 mL, 511 mmol). The reaction mixture was warmed to 48° C. for 1 hr, then diluted with isopropyl acetate (190 mL) and cooled to RT for a further 18 hr, during which time a precipitate formed. The precipitate was isolated by filtration, washed with isopropyl acetate and then dried in vacuo at 40° C. to afford the title compound, Compound (1) as a white solid (anhydrous free base, polymorphic form A) (16.5 g, 92%); $R^t$ 2.74 min (Method 2); m/z 584 (M+H)$^+$ (ES$^+$); $^1$H NMR (400 MHz, DMSO-d$_6$) δ: 1.30 (9H, s), 2.41 (3H, s), 6.43 (1H, s), 6.58 (1H, d), 6.78 (1H, t), 6.97 (2H, t), 7.28 (2H, br m), 7.39 (2H, d), 7.40 (1H, d), 7.49 (2H, d), 7.56 (1H, m), 7.63 (1H, m), 7.82 (1H, dd), 7.95 (1H, d), 8.10 (1H, d), 8.40 (1H, d), 8.77 (1H, s), 9.16 (1H, br s), 9.50 (1H, br s).

Example 2—Summary of In Vitro and In Vivo Screening Results

The in vitro profile of Compound (I) disclosed herein, as determined using the protocols described above, are presented below (Tables 4a-f) in comparison with a structurally related Reference Compound which is N-(4-(4-(3-(3-tert-butyl-1-p-tolyl-1H-pyrazol-5-yl)ureido) naphthalen-1-yloxy)pyridin-2-yl)-2-methoxyacetamide, which has been previously described as a potent anti-inflammatory agent with anti-viral activity (Ito, K. et al., WO 2010/112936, PCT/GB2010/050575, 7 Oct. 2010 and Ito, K. et al., WO 2010/067130, PCT/GB2009/051702, 17 Jun. 2010).

The compound of the present invention demonstrates a very similar inhibitory profile to the Reference Compound in the range of kinase enzyme assays with the marked exception of the inhibitory activity of Compound (I) against the enzyme GSK3α, which is very much weaker than the Reference Compound (Table 4a).

TABLE 4a

| p38 MAPK, c-Src, Syk and GSK3 α Enzyme Profile of Compound (I) | | | | | |
|---|---|---|---|---|---|
| Test | IC$_{50}$ Values for Enzyme Inhibition (nM) | | | | |
| Compound | p38 MAPKα | p38 MAPKγ | c-Src | Syk | GSK3α |
| Compound (I) | 60 | 3739 | 22 | 334 | >17000 |
| Reference Compound | 12 | 344 | 5 | 42 | 45 |

The kinase binding profile of Compound (I) of the present invention was also compared with the Reference Compound against p38 MAPK, HCK, cSrc, Syk, and GSK3α/β. Compound (I) displayed a very different phenotype, demonstrating profound inhibition of binding versus p38MAPK, HCK, cSrc and Syk kinases, without significant effect against GSK3α (Table 4b).

TABLE 4b

| Comparison of the Enzyme Binding Profile of Compound (I) with the Reference Compound. | | | | | | | |
|---|---|---|---|---|---|---|---|
| Test | Kd value for kinase binding (nM) | | | | | | |
| Compound | p38 MAPKα | p38 MAPKγ | HCK | cSrc | Syk | GSK3α | GSK3β |
| Compound (I) | 20 | 43 | 8 | 10 | 14 | 20000 | 1200 |
| Reference compound | 1 | 5 | 5 | 4 | 9 | 180 | 24 |

The compound of the present invention demonstrates a similar profile to the Reference Compound in cellular assays that reveal anti-inflammatory properties against endotoxin mediated release of both TNFα and IL-8 (Table 4c). The profiles of the compounds are also similar in cellular systems measuring their effects on respiratory virus replication (HRV induced ICAM1 and CPE expression and RSV stimulated expression of F-protein) as well as virus-induced inflammation (HRV evoked release of IL-8; Table 4d).

TABLE 4c

Inhibition of LPS Induced TNFα and IL-8 Release and PolyIC Induced ICAM-Expression for Compound (I)

| Test Compound | LPS Induced Release (nM) | | | PolyIC/ |
|---|---|---|---|---|
| | TNFα | | IL-8 $IC_{50}$ | ICAM1 (nM) |
| | $IC_{50}$ (THP1) | $REC_{50}$ (dU937) | (dU937) | $IC_{50}$ (BEAS2B) |
| Compound (I) | 3.4 | 2.3 | 2.2 | 10.2 |
| Reference Compound | 13 | 0.13 | 1.3 | 2.1 |

TABLE 4d

The Effect of Compound (I) on HRV-16 Propagation (CPE) and Inflammation (Expression of ICAM-1 and IL-8 Release) and on RSV Propagation (F-Protein Expression).

| Test Substance | $IC_{50}$ Values (nM) for HRV Stimulated Release/Expression | | | $IC_{50}$ Values (nM) for RSV Stimulated Expression |
|---|---|---|---|---|
| | IL-8 (BEAS2B) | ICAM1 (BEAS2B) | CPE (MRC5) | F-Protein (HBEC) |
| Compound (I) | 0.036 | 0.023 | 17.1 | 15.4 |
| Reference Compound | 0.065 | 0.37 | 4.7 | 22.0 |

The compound of the present invention demonstrated higher efficacy in pro-inflammatory cytokine production in sputum macrophage and bronchial epithelial cells obtained from COPD patients, which were largely insensitive to fluticasone propionate, a corticosteroid, (Table 4e).

TABLE 4e

The Effect of Compound (I) and Fluticasone propionate on pro-inflammatory cytokine release in sputum macrophages and bronchial epithelial cell from COPD patients.

| | | $IC_{50}$ values (nM) and/or E max (% in parentheses)[1] for Test Substance Indicated | |
|---|---|---|---|
| Cells Type | Cytokine | Compound (I) | Fluticasone Propionate |
| Sputum Macrophage | IL-6 | 43 (79) | (26) |
| | IL-8 | 68 (64) | (19) |
| | TNFα | 17 (86) | (18) |
| | MIP1α | 7.5 (89) | (20) |
| Bronchial Epithelial Cell | IL-6 | 1.7 (100) | (38) |
| | IL-8 | 0.85 (100) | (17) |

[1]E-max values (maximum inhibiton) were calculated as the % inhibition obtained at 0.1 µg/mL However, advantageously, Compound (I) shows markedly less activity in assay systems that measure its impact on cell viability and cell division (mitosis) indicating that the compound is likely to possess a superior therapeutic index over the Reference Compound (Table 4f).

TABLE 4f

Effect of Compound (I) on Cellular Viability and Cell Division

| | MTT Assay[1] Cell viability at time point indicated in d-U937 Cells | | Mitosis Assay % Inhibition at 5 µg/mL |
|---|---|---|---|
| Test Substance | 4 h | 24 h | in PBMC Cells |
| Compound (I) | −ve | −ve | 31.3 |
| Reference Compound | −ve | +ve | 87.8 |

[1]Cell viability screen: −ve and +ve indicate the value is below and above respectively, the no significant effect threshold defined as 30% inhibition at 1 µg/mL at the time point indicated.

Treatment of mice with Compound (I) was found to produce a dose dependent inhibition on LPS-induced neutrophil accumulation and a time course experiment revealed that the drug substance had a long duration of action (Table 5).

TABLE 5

The Effects of Treatment with Compound (I) on LPS-Induced Airway Neutrophilia in Mice.

| Compound (I) | Neutrophil numbers in BALF (×10⁵/mL) at pre-dose time indicated (% inhibition)[1] | | |
|---|---|---|---|
| (mg/mL) | 2 hr | 8 hr | 12 hr |
| Vehicle | 18.9 ± 2.5 | — | — |
| 0.05 | 15.6 ± 2.1 (18) | — | — |
| 0.2 | 9.8 ± 1.6 (48) | — | — |
| 1.0 | 4.4 ± 0.89 (77) | 9.9 ± 1.8 (48) | 18.3 ± 2.3 (4) |

[1]N = 8 per group

The result of treatment with Compound (I) on macrophage and neutrophil accumulation in BALF in the mouse cigarette smoke model was investigated (Table 6a). The cigarette smoke model used for this study is reported to be a corticosteroid refractory system, (Medicherla S. et al., *J. Pharmacol. Exp. Ther.*, 2008, 324(3):921-9.) and it was confirmed that fluticasone propionate did not inhibit either neutrophil or macrophage accumulation into airways at 1.75 µg/mouse (35 µL, bid, i.n.), the same dose that produced >80% inhibition of LPS-induced neutrophil accumulation.

Treatment of mice with Compound (I) was found to produce a dose-dependent inhibition on both macrophage and neutrophil accumulation in BALF induced by cigarette smoke.

TABLE 6A

The Effects of Treatment with Compound (I) on Tobacco Smoke in Mice.

| Treatment | Cell numbers in BALF × 10⁴/mL (% inhibition) | |
|---|---|---|
| Compound (I) (µg/mL) | Macrophage | Neutrophil |
| Vehicle + Air | 4.3 ± 0.45 | 2.6 ± 0.21 |
| Vehicle + Tobacco Smoke | 14.4 ± 0.33 | 13.7 ± 0.31 |
| 0.32 | 13.3 ± 0.20 (11) | 12.4 ± 0.32 (12) |
| 1.6 | 11.6 ± 0.42 (28) | 10.5 ± 0.06 (29) |
| 8.0 | 10.1 ± 0.42 (43) | 9.1 ± 0.28 (41) |
| 40 | 7.9 ± 0.20 (64) | 7.9 ± 0.34 (52) |

The data for cell numbers are shown as the mean ± SEM, N = 5

Treatment of mice with Compound (I) also inhibited cigarette smoke induced CXCL1 (KC) production in BALF in a dose-dependent manner (Table 6b).

TABLE 6B

The Effects of Treatment with Compound (I) on CXCL1
(KC) release in BALF on Tobacco Smoke in Mice.

| Treatment<br>Compound (I) (μg/mL) | CXCL1 in BALF<br>pg/mL (% inhibition) |
|---|---|
| Vehicle + Air | 8.2 ± 0.30 |
| Vehicle + Tobacco Smoke | 13.6 ± 1.69 |
| 0.32 | 13.6 ± 1.69 (0) |
| 1.6 | 12.2 ± 0.96 (26) |
| 8.0 | 11.4 ± 0.15 (41) |
| 40 | 9.5 ± 0.84 (76) |

The data for CXCL level are shown as the mean ± SEM, N = 5

In summary, these results suggest that the Compound (I) has similar anti-inflammatory properties to the Reference Compound disclosed above and, advantageously, is associated with a superior therapeutic index.

Example 3: Preparation of Compound (I) as the Anhydrous Free Base in Solid, Crystalline, Polymorphic Form B Compound (I) (398 g, in polymorphic form A) was taken up in acetone (3.98 L) and the solution heated to 50° C. NORIT A SUPRA (19.9 g, an activated carbon) and diatomaceous earth, flux-calcined (3.98 g; a filter agent) were then added and the mixture was heated to reflux (56° C.) for 15 min. The mixture was filtered and the resulting solid was washed with acetone (100 mL). The combined filtrate and washing acetone was warmed to reflux (56° C.), and 900 mL of solvent was removed via distillation under atmospheric pressure at 56° C. The mixture was cooled to 50° C. and water (398 mL) was then added over a period of 1 hr whilst the temperature was maintained at 50° C. After an additional 30 min at 50° C. the heterogeneous mixture was cooled to 20° C. over 6 h and then stirred at 20° C. for 10 hr. The resulting product was filtered and the cake was washed with acetone (318 mL). The product was dried in vacuo at 45° C. for 20 hr to produce Compound (I) as the anhydrous free base in solid, crystalline, polymorphic form B (240.9 g; 60.5% yield).

The above method may optionally be adapted to facilitate crystallization with seeding.

Example 3a: Preparation of Compound (I) as the Anhydrous Free Base in Solid, Crystalline, Polymorphic Form B Containing Reduced Residual Solvent Optionally, Compound (I) as the anhydrous free base in solid, crystalline, polymorphic form B, as prepared according to the procedure described above (Example 3) or a similar method, may be re-slurried from water in order to reduce residual solvent as follows:

Compound (I) as the anhydrous free base in solid, crystalline, polymorphic form B (230 g, as prepared according to Example 3) was suspended in deionized water (2.30 L) and was stirred at 20° C. for 4 hr. The mixture was filtered and the product was washed with deionized water (2×115 mL) and was then dried at 45° C. in vacuo to produce Compound (I) as the anhydrous free base in solid, crystalline, polymorphic form B containing reduced residual solvent (227 g, 98.7%).

Example 4: Micronization of Compound (I) as the Anhydrous Free Base in Solid, Crystalline, Polymorphic Form B Micronized crystalline polymorphic form B of Compound (I) as the anhydrous free base was prepared using a jet mill micronization device (1.5 bar using a manual feeder with an injector pressure of 1.5 bar) (manufactured by Hosokawa Alpine). The particle size distribution was measured using laser diffraction (Malvern Mastersizer 2000S instrument). Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively. Micronized crystalline polymorphic form B of Compound (I) as the anhydrous free base had the following particle size distribution: $D_{10}$ of 0.850 μm; $D_{50}$ of 1.941 μm and $D_{90}$ of 4.563 μm.

Example 5: XRPD Analysis of Compound (I) as the Anhydrous Free Base in Solid, Crystalline, Polymorphic Forms A and B XRPD analysis of Compound (I) as the anhydrous free base in solid crystalline polymorphic forms A and B (polymorphic form B was micronized following the procedure of Example 4) was undertaken using the method described in General Procedures. The resulting diffraction patterns are shown in FIGS. 1 and 2 respectively. Both XRPD patterns showed diffraction peaks without the presence of a halo, thereby indicating that both materials are crystalline. Peaks and their intensities are listed below (Table 7a and Table 7b).

TABLE 7a

Characteristic XRPD peaks and their intensities for Compound (I) as the anhydrous free base in solid, crystalline, form A
XRPD Peaks

| 2-Theta Values[1] | Intensities |
|---|---|
| 7.8 | 19.7 |
| 8.7 | 20.8 |
| 10.3 | 22.6 |
| 11.2 | 23.1 |
| 12.4 | 24.6 |
| 15.2 | 25.5 |
| 16.2 | 26.7 |
| 17.5 | 27.4 |

[1]Values are ± 0.2 degrees

TABLE 7B

Characteristic XRPD peaks for Compound (I) as the anhydrous free base in solid crystalline form B, post micronization.
XRPD peaks

| 2-Theta Values[1] | Intensities |
|---|---|
| 3.9 | 16.7 |
| 6.1 | 18.3 |
| 7.7 | 18.7 |
| 8.6 | 19.9 |
| 10.9 | 20.9 |
| 11.8 | 22.0 |
| 12.7 | 22.6 |

TABLE 7B-continued

Characteristic XRPD peaks for Compound (I) as the anhydrous
free base in solid crystalline form B, post micronization.
XRPD peaks

| 2-Theta Values[1] | Intensities |
|---|---|
| 14.3 | 25.2 |
| 15.9 | 28.9 |

[1]Values are ± 0.2 degrees

Example 6: Melting Point Determination of Compound (I) as the Anhydrous Free Base in Solid, Crystalline, Polymorphic Forms A and B The melting points of Compound (I) as the anhydrous free base in solid crystalline polymorphic forms A and B (the latter post micronization) were obtained using differential scanning calorimetry (DSC), as described in the General Procedures. Polymorphic form A melted at 191.6° C. and polymorphic form B melted at 214.0° C. From the DSC data it was calculated that form B had a higher heat of fusion than form A. Since form B also has a higher melting point than form A, this indicates that polymorphic forms A and B are monotropic related, meaning that higher melting polymorphic form B will be more stable than lower melting polymorphic form A, at all temperatures. As such, it can be expected that polymorphic form B is thermodynamically more stable than polymorphic form A.

Example 7: Thermal Analysis of Compound (I) as the Anhydrous Free Base in Solid, Crystalline, Polymorphic Form B, Post Micronization Thermal analysis of Compound (I) as the anhydrous free base in crystalline polymorphic form B (micronized) was undertaken using TGA, DVS, XRPD analysis, IR spectroscopy and DSC as described in General Procedures. Where appropriate, a sample at ambient temperature and relative humidity (reference sample/"0 days") was compared with samples stored at various temperatures and relative humidities (comparative samples).

Figure 3:
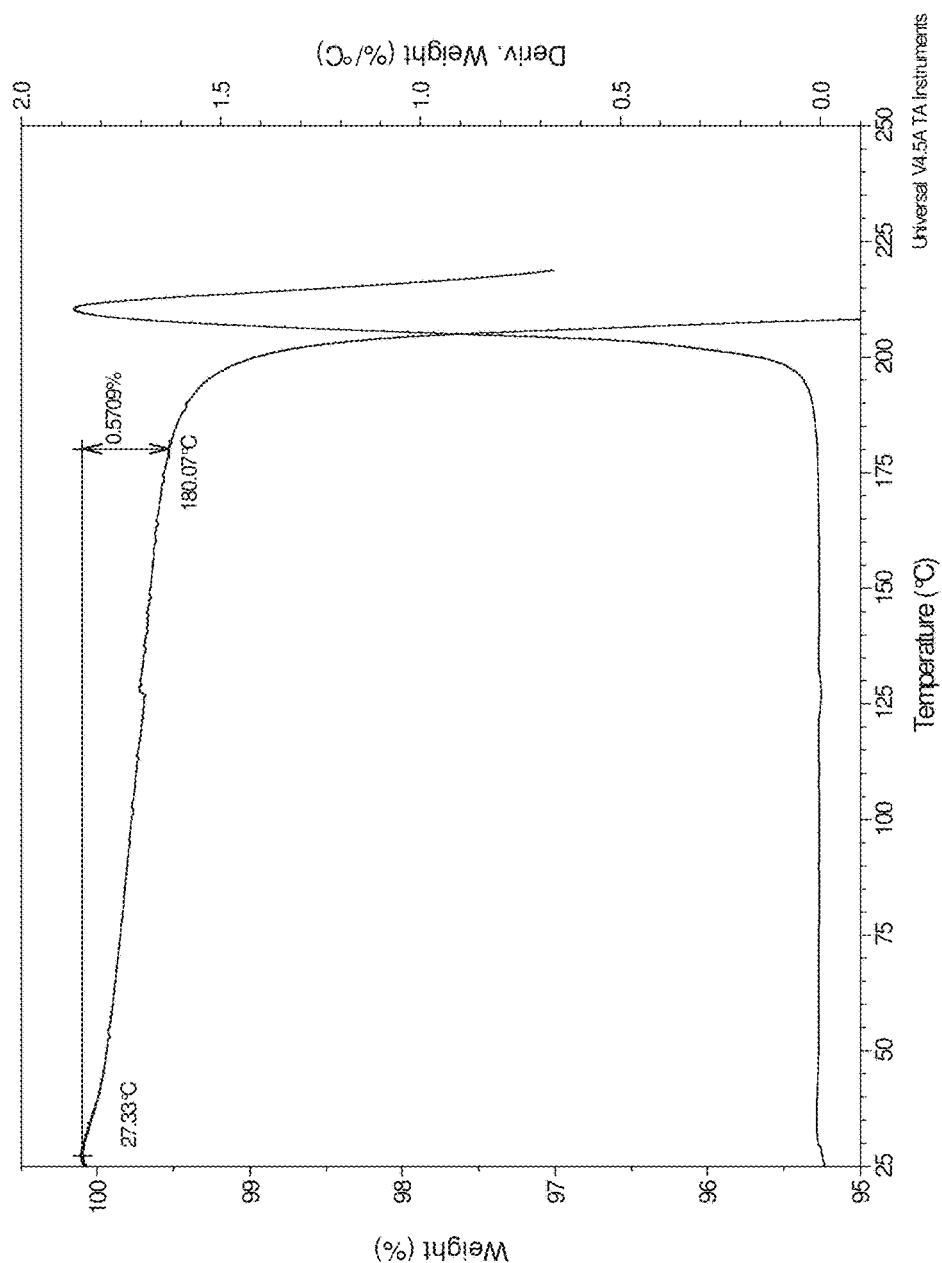
FIG. 3 reveals the results of thermogravimetric analysis of a sample of Compound (I) as the anhydrous free base in solid crystalline polymorphic form B, post micronization.

Thermogravimetric Analysis:

The reference sample (t=0) and the comparative samples that were exposed prior to analysis to different storage conditions, were heated at a rate of 20° C./min from RT to 300° C. The TGA curve of the reference sample (t=0) is illustrated in FIG. 3 and the results for all samples are summarised below (Table 7). As can be seen from FIG. 3, a weight loss of 0.6% was observed in the temperature range from RT to 180° C., which was due to solvent evaporation. The weight loss that occurred above 180° C. was due to evaporation and decomposition of the product. Comparing this weight loss profile with those of the comparative samples in Table 7, no significant differences were observed.

Figure 4:
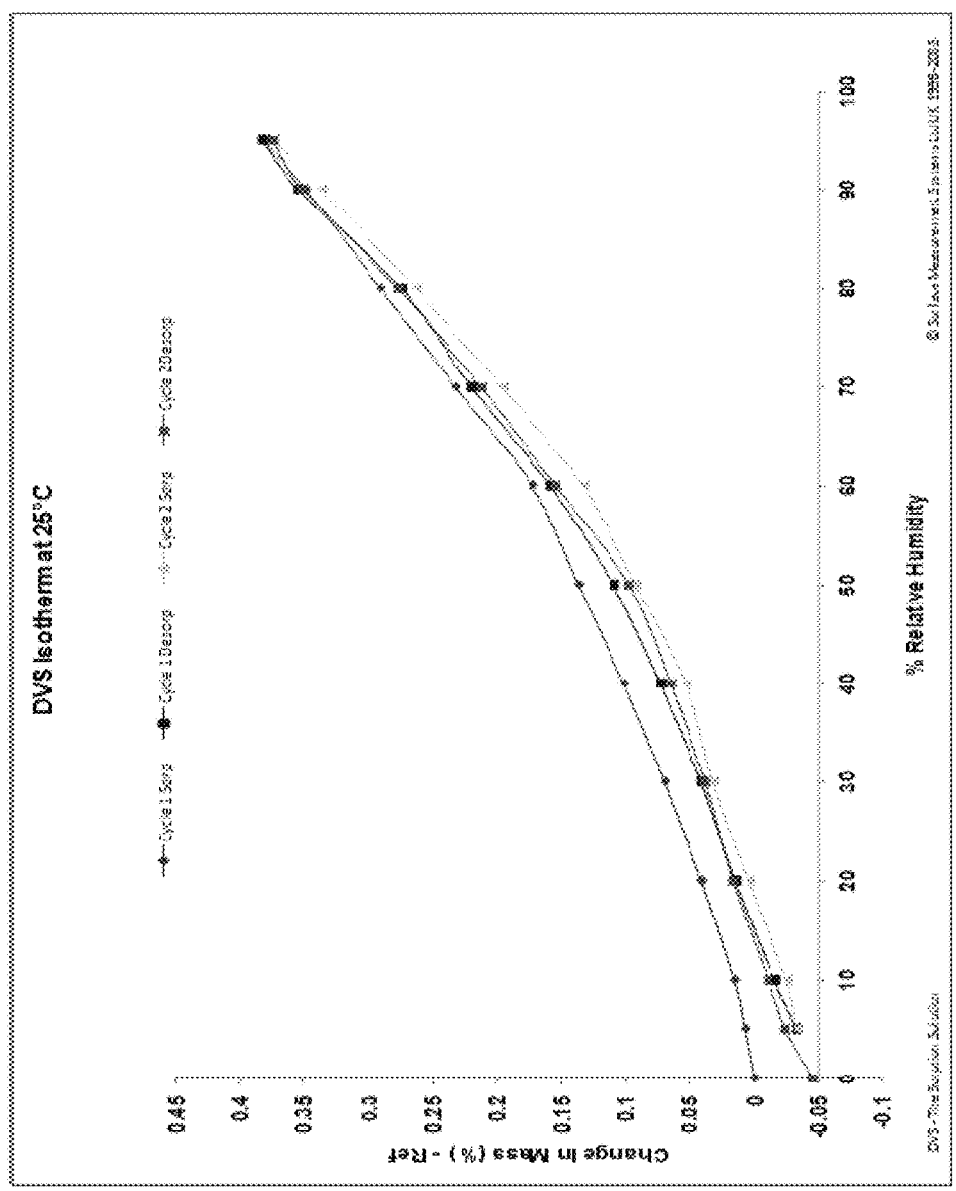
FIG. 4 represents dynamic vapour sorption (DVS) isotherm plots derived from samples of Compound (I) as the anhydrous free base in solid crystalline polymorphic form B post micronization.
Figure 5:
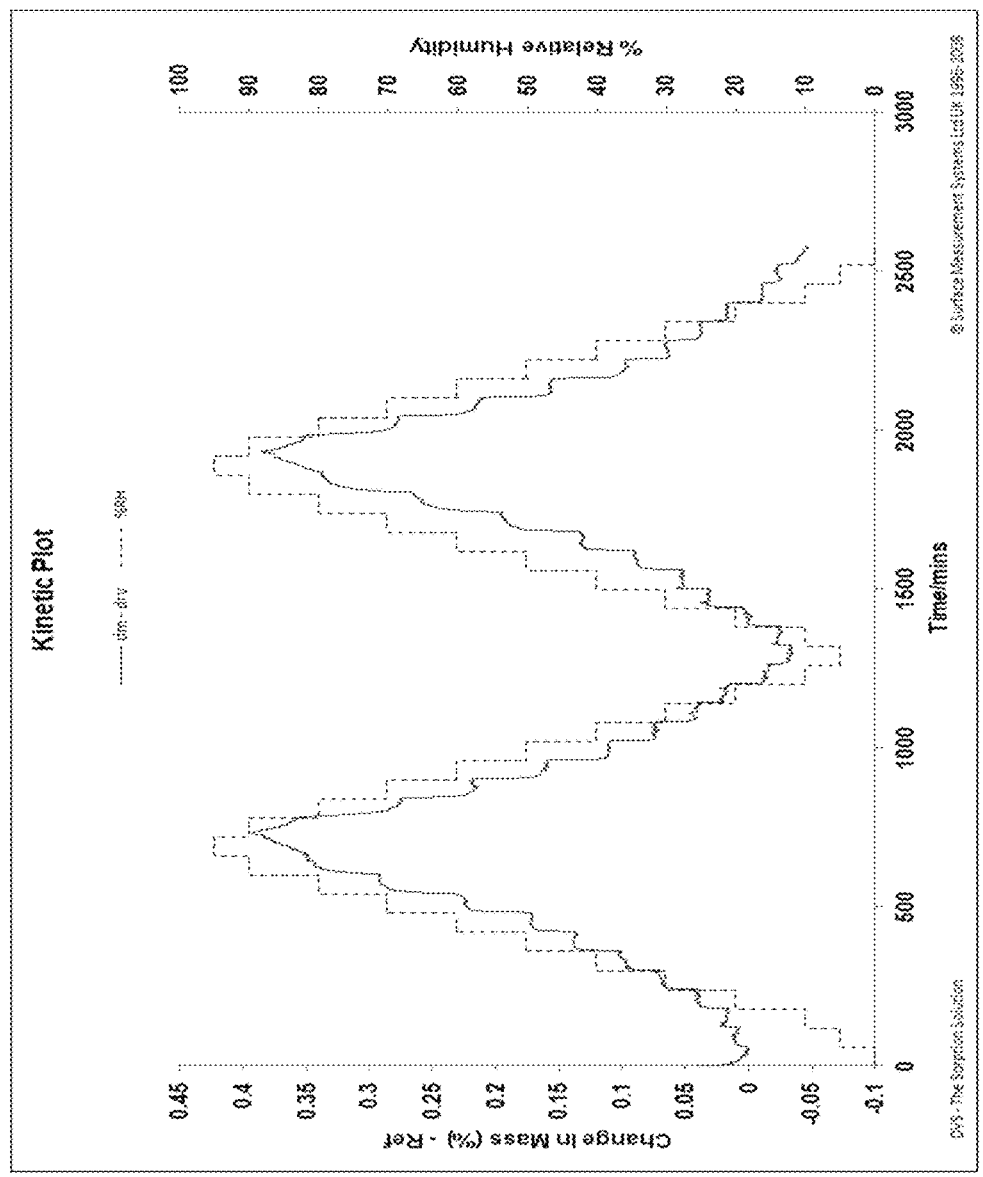
FIG. 5 represents the results of a hysterisis experiment conducted on Compound (I) as the anhydrous free base in solid, crystalline, polymorphic form B, post micronization, to determine the degree and rate of moisture absorption/desorption with time against changes in relative humidity.

Dynamic Vapour Sorption:

The DVS isotherm plot for the micronized reference sample is illustrated in FIG. 4 and the DVS change in mass plot for the micronized reference sample is illustrated in FIG. 5. During the initial drying step, no weight loss was registered and the product showed no hygroscopic behavior. The product adsorbed up to 0.4% moisture depending on the atmospheric humidity. The product was found to dry out completely and remained in the same crystalline solid state (form B) during the test, as evidenced by the IR spectrum and XRPD pattern being substantially the same before and after the DVS analysis.

Figure 6:
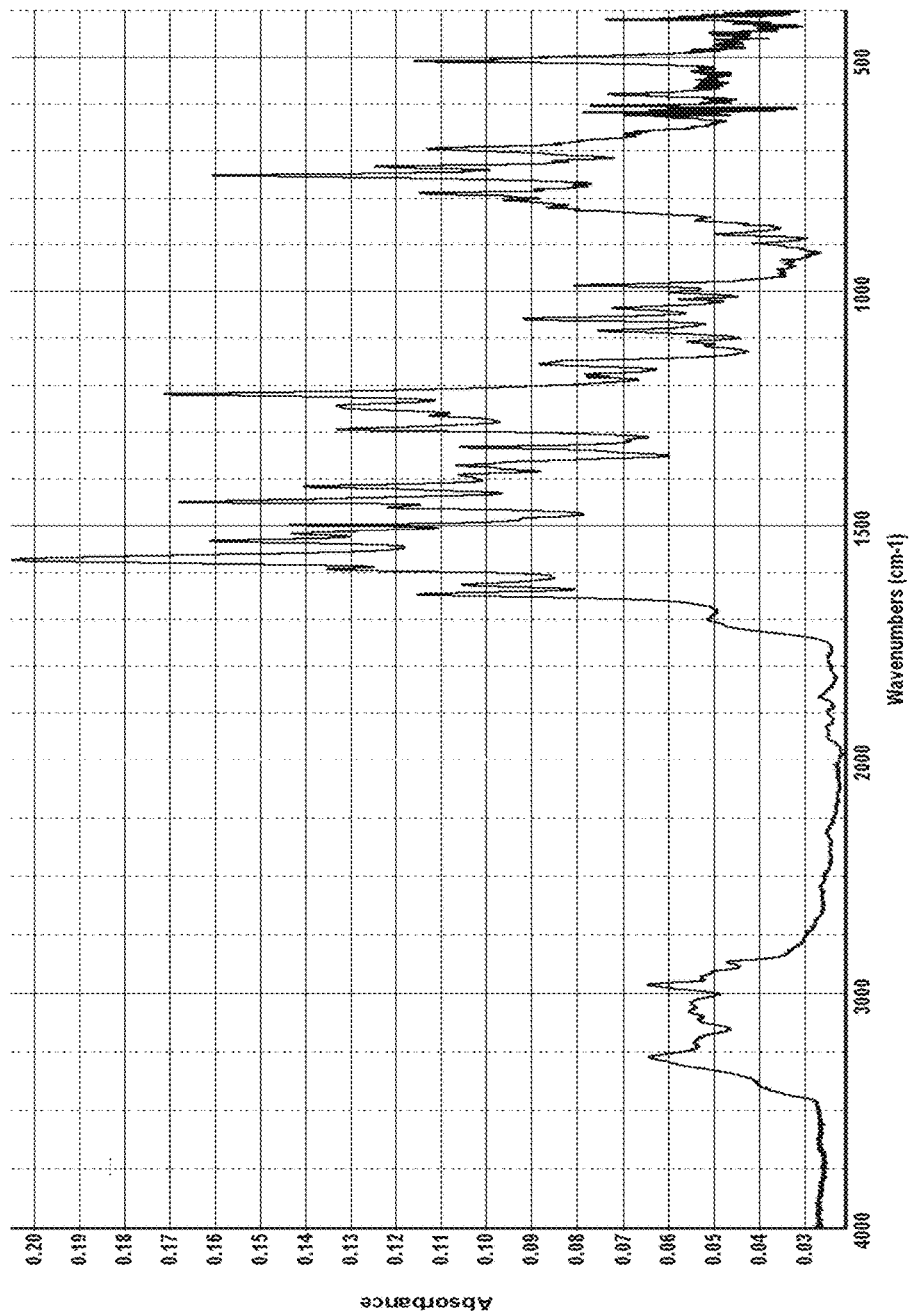
FIG. 6 is the infrared (IR) spectrum obtained from a sample of Compound (I) as the anhydrous free base in solid crystalline polymorphic form B post micronization.

XRPD Analysis and IR Spectroscopy:

The XPRD diffraction pattern of the reference sample (t=0) is illustrated in FIG. 2 and the IR trace is illustrated in FIG. 6. The diffraction pattern and IR trace were compared with those of the comparative samples (exposed to different storage conditions) and the results are summarised in Table 7. The diffraction patterns and IR traces were identical for all samples.

Figure 7:
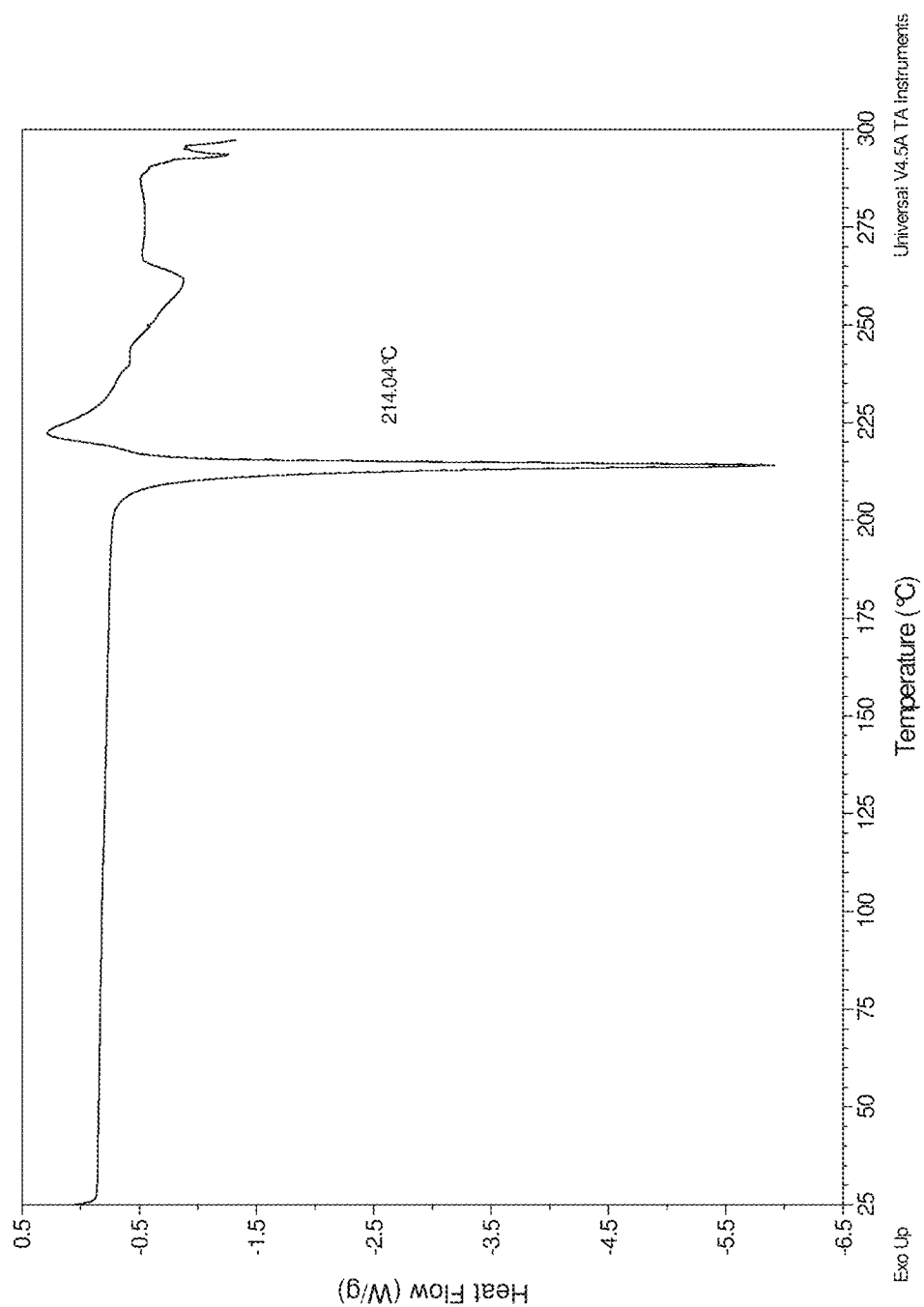
FIG. 7 shows thermal analysis of a sample of Compound (I) as the anhydrous free base in solid crystalline polymorphic form B (micronized) by differential scanning calorimetry (DSC).

Differential Scanning Calorimetry:

The reference sample (t=0) and comparative samples, previously exposed to different storage conditions, were heated at a rate of 10° C./min from 25° C. to 300° C. The DSC curve of the reference sample is illustrated in FIG. 7 and the results for all samples are summarised below (Table 8). From FIG. 7, it is evident that the reference sample melted with decomposition at 214.0° C.

TABLE 8

Thermal analysis of Compound (I) as the anhydrous free base
in solid crystalline polymorphic form B post micronization.

| Storage Conditions | TGA <100° C. | TGA <180° C. | XRD[1,2] | IR | DSC[3] | Appearance |
|---|---|---|---|---|---|---|
| T = zero | | 0.6 | Cryst. Ref | Cryst. Ref | 214 | off-white |
| 1 week/ 80° C. | NT | NT | ~Ref | ~Ref | NT | off-white |
| 1 week/ 70° C./ 75% RH | NT | NT | ~Ref | ~Ref | NT | off-white |
| 4 weeks/RT/ <5% RH | 0.8 | 0.5 | ~Ref | ~Ref | 214 | off-white |
| 4 weeks/RT/ 56% RH | 0.5 | 0.4 | ~Ref | ~Ref | 214 | off-white |
| 4 weeks/RT/ 75% RH | 0.9 | 0.5 | ~Ref | ~Ref | 214 | off-white |
| 4 weeks/ 50° C. | 1.3 | 0.5 | ~Ref | ~Ref | 214 | off-white |
| 4 weeks/ 40° C./ 75% RH | 0.8 | 0.3 | ~Ref | ~Ref | 214 | off-white |

[1]Cryst.: crystalline;
[2]~Ref: pattern identical with reference sample,
[3]max (° C.);
NT: Not tested in this assay In summary, it is evident that Compound (I) as the anhydrous free base in solid, crystalline, polymorphic form B has good physical stability.

Example 8: HPLC Analysis of Compound (I) as the Anhydrous Free Base in Solid, Crystalline, Polymorphic Form B Post Micronization The chemical stability of Compound (I) as the anhydrous free base in solid, crystalline, polymorphic form B, following micronization, was determined by comparing a sample maintained at ambient temperature and relative humidity (reference sample) with samples stored at various temperatures and relative humidities as set out hereinabove (the comparative samples, Table 8). The reference and comparative samples were then analyzed by HPLC using the method described in General Procedures and by visual inspection. The results from this study (data summarised in Table 9) reveal that Compound (I), prepared as the anhydrous free base in solid, crystalline, polymorphic form B is chemically stable although some sensitivity to light was observed.

TABLE 9

Chemical stability of Compound (I) as the anhydrous free base in solid, crystalline, polymorphic form B, post micronization.

| Storage Conditions | Sum of impurities by HPLC (%)[1] | | Appearance[1] | |
|---|---|---|---|---|
| | 1 week | 4 weeks | 1 week | 4 weeks |
| T = zero | 0.66 | NT | off-white | NT |
| 0.3 day, ICH light[2] | 1.44 | NT | off-white | NT |
| 80° C. | 0.73 | NT | off-white | NT |
| 70° C./75% RH | 0.73 | NT | off-white | NT |
| 40° C./75% RH | 0.66 | 0.68 | off-white | off-white |
| 50° C. | 0.69 | 0.66 | off-white | off-white |
| RT/<5% RH | NT | 0.67 | NT | off-white |
| RT/56% RH | NT | 0.67 | NT | off-white |
| RT/75% RH | NT | 0.67 | NT | off-white |

[1]NT in this assay system;
[2]Stimulated daylight: light cabinet 700 W/m².

Example 9—Preparation of Pharmaceutical Formulations

An exemplary pharmaceutical formulation of the invention would consist of 0.4 wt. % of Compound (I) (as the anhydrous free base in solid crystalline polymorphic form B), 98.6 wt. % lactose monohydrate (inhalation grade) and 1.0 wt. % magnesium stearate, wherein the wt. % of all components is based on the weight of the dry pharmaceutical formulation.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A dry powder pharmaceutical formulation for inhalation comprising: a compound of formula (I)

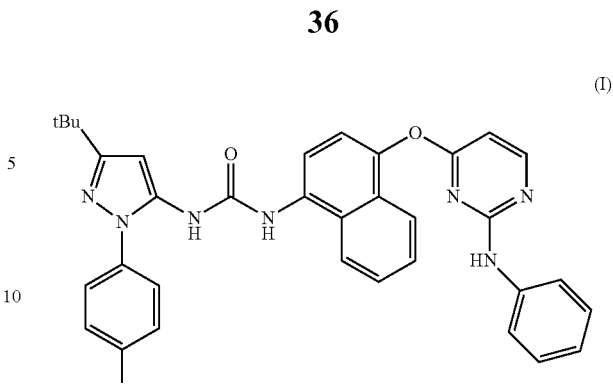

(I)

or a pharmaceutically acceptable salt thereof, including all stereoisomers and tautomers thereof.

2. A dry powder pharmaceutical formulation according to claim 1, wherein the compound of formula (I) is in its free base form.

3. A dry powder pharmaceutical formulation according to claim 1, wherein the compound of formula (I) is in its anhydrous free base form.

4. A dry powder pharmaceutical formulation according to claim 1, wherein the compound of formula (I) is the anhydrous free base in solid crystalline form.

5. A dry powder pharmaceutical formulation according to claim 4, wherein the compound of formula (I) is the anhydrous free base in solid crystalline form having an X-ray powder diffraction pattern containing one, two, three, four, five, six or seven peaks selected from (±0.2) 10.3, 15.2, 17.5, 23.1, 24.6, 26.7 and 27.4 degrees 2-theta.

6. A dry powder pharmaceutical formulation according to claim 4, wherein the compound of formula (I) is the anhydrous free base in solid crystalline form having an X-ray powder diffraction pattern substantially as shown in FIG. 2 (Form B).

7. A dry powder pharmaceutical formulation according to claim 4, wherein the compound of formula (I) is the anhydrous free base in solid crystalline form having an X-ray powder diffraction pattern containing one, two, three, four, five, six, seven or all eight peaks selected from (±0.2) 3.9, 6.1, 11.8, 14.3, 16.7, 18.3, 18.7 and 28.9 degrees 2-theta.

8. A dry powder pharmaceutical formulation according to claim 1, further comprising lactose.

9. A dry powder pharmaceutical formulation according to claim 8, wherein the lactose is lactose monohydrate.

10. A dry powder pharmaceutical formulation according to claim 1 further comprising a particulate metal salt of stearic acid.

11. A dry powder pharmaceutical formulation according to claim 10, wherein the particulate metal salt of stearic acid is magnesium stearate.

* * * * *